United States Patent
Ohtsuka et al.

(10) Patent No.: US 12,387,474 B2
(45) Date of Patent: Aug. 12, 2025

(54) INTRAORAL CAMERA SYSTEM, TOOTH IDENTIFICATION METHOD, CONTROL METHOD, AND RECORDING MEDIUM

(71) Applicant: Panasonic Intellectual Property Management Co., Ltd., Osaka (JP)

(72) Inventors: Yoshio Ohtsuka, Osaka (JP); Masato Izawa, Osaka (JP); Tomoki Ogawa, Osaka (JP); Toshiyuki Nakashima, Nara (JP); Masayuki Aihara, Osaka (JP); Kazuhiro Funamoto, Hyogo (JP); Tadashi Miki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 225 days.

(21) Appl. No.: 18/033,713

(22) PCT Filed: Feb. 17, 2022

(86) PCT No.: PCT/JP2022/006358
§ 371 (c)(1),
(2) Date: Apr. 25, 2023

(87) PCT Pub. No.: WO2022/176941
PCT Pub. Date: Aug. 25, 2022

(65) Prior Publication Data
US 2023/0397805 A1     Dec. 14, 2023

(30) Foreign Application Priority Data
Feb. 22, 2021 (JP) .................. 2021-026076

(51) Int. Cl.
G06V 10/82     (2022.01)
A61B 1/247    (2006.01)
A61C 19/04    (2006.01)

(52) U.S. Cl.
CPC ............ *G06V 10/82* (2022.01); *A61B 1/247* (2013.01); *A61C 19/04* (2013.01)

(58) Field of Classification Search
None
See application file for complete search history.

(56) References Cited

U.S. PATENT DOCUMENTS 9,757,020 B1   9/2017  Elazar et al.
10,898,306 B2  1/2021  Schmid et al.
(Continued)

FOREIGN PATENT DOCUMENTS

JP   2019-517864 A   6/2019
JP   2019-536553 A   12/2019
(Continued)

OTHER PUBLICATIONS

Oktay, A.—"Human Identification with Dental Panoramic Radiographic Images"—IET Biometrics 2018—pp. 349-355 (Year: 2018).*
(Continued)

*Primary Examiner* — Bernard Krasnic
(74) *Attorney, Agent, or Firm* — Rimon P.C.

(57) ABSTRACT

An intraoral camera system includes an imaging unit that generates image data by capturing an image of a tooth inside the mouth of a user, an area detector that detects the orientation of the imaging unit according to output by a multi-axis acceleration sensor and detects, according to the orientation detected, an area whose image is being captured by the imaging unit from among areas inside the mouth, the areas being determined by dividing a dentition into sections, and an identifier that narrows candidates which are combinations of tooth types and tooth positions down to fewer candidates to be used, according to the image data and the
(Continued)

area detected, and identifies the type and the position of the tooth according to the narrowed candidates and the image data.

14 Claims, 15 Drawing Sheets

(56) References Cited

U.S. PATENT DOCUMENTS

| | | | |
|---|---|---|---|
| 2020/0015943 | A1 | 1/2020 | Reynard et al. |
| 2020/0320685 | A1* | 10/2020 | Anssari Moin .......... G06N 3/08 |
| 2022/0117480 | A1 | 4/2022 | Kaji et al. |

FOREIGN PATENT DOCUMENTS

| | | |
|---|---|---|
| JP | 2020-096797 A | 6/2020 |
| JP | 2020-516335 A | 6/2020 |
| WO | 2017/205294 A1 | 11/2017 |
| WO | 2018/098107 A1 | 5/2018 |
| WO | 2018/167530 A1 | 9/2018 |
| WO | 2020/145225 A1 | 7/2020 |
| WO | 2020/161301 A1 | 8/2020 |

OTHER PUBLICATIONS

Extended European Search Report dated Jun. 25, 2024 issued in the corresponding European Patent Application No. 22756259.2.
International Search Report issued on May 17, 2022 in International Patent Application No. PCT/JP2022/006358, with English translation.

* cited by examiner

| | Imaging direction | | |
|---|---|---|---|
| | Buccal side | Lingual side | Top |
| Maxillary front (right) central incisor | | | |
| Maxillary front (right) canine | | | |
| Maxillary right first molar | | | |

INTRAORAL CAMERA SYSTEM, TOOTH IDENTIFICATION METHOD, CONTROL METHOD, AND RECORDING MEDIUM

CROSS-REFERENCE OF RELATED APPLICATIONS

This application is the U.S. National Phase under 35 U.S.C. § 371 of International Patent Application No. PCT/JP2022/006358, filed on Feb. 17, 2022, which in turn claims the benefit of Japanese Patent Application No. 2021-026076, filed on Feb. 22, 2021, the entire disclosures of which Applications are incorporated by reference herein.

TECHNICAL FIELD

The present disclosure relates to an intraoral camera system and a tooth identification method.

BACKGROUND ART

Patent Literature (PTL) 1 discloses a method using an estimation model including a neural network, as a method of identifying the type of a tooth inside a mouth.

CITATION LIST

Patent Literature

[PTL 1] Japanese Unexamined Patent Application Publication No. 2020-96797

SUMMARY OF INVENTION

Technical Problem

It is desirable that the accuracy of identification be improved in such an intraoral camera system that identifies the type of a tooth.

In view of this, the present disclosure aims to provide an intraoral camera system and a tooth identification method which are capable of improving the accuracy of tooth identification.

Solution to Problem

An intraoral camera system according to one aspect of the present disclosure includes an imaging unit that generates image data by capturing an image of a tooth inside the mouth of a user, an orientation detector that detects the orientation of the imaging unit according to output by a multi-axis acceleration sensor, an area detector that detects, according to the orientation detected, an area whose image is being captured by the imaging unit from among areas inside the mouth, the areas being determined by dividing a dentition into sections, and an identifier that narrows candidates which are combinations of tooth types and tooth positions down to fewer candidates to be used, according to the image data and the area detected, and identifies the type and position of the tooth according to the fewer candidates narrowed down and the image data.

Advantageous Effects of Invention

The present disclosure can provide an intraoral camera system and a tooth identification method which are capable of improving the accuracy of tooth identification.

DESCRIPTION OF EMBODIMENTS

Figure 1:
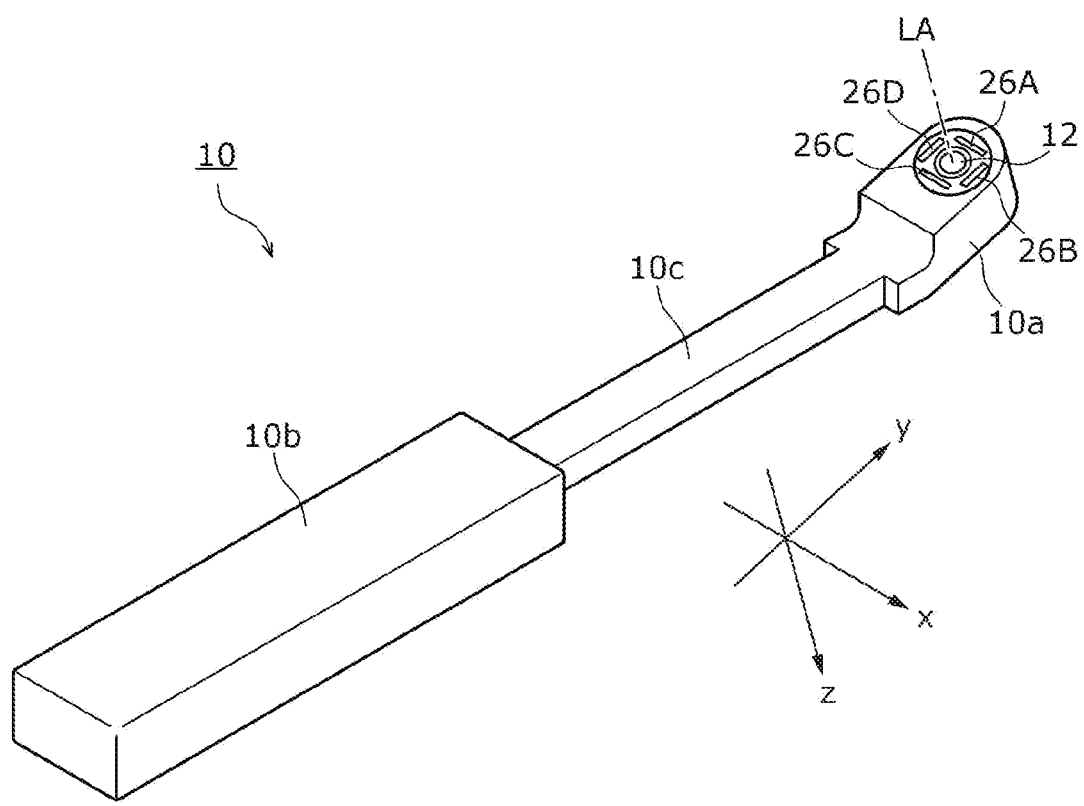
FIG. 1 is a perspective view of the intraoral camera of an intraoral camera system according to an embodiment.

An intraoral camera system according to one aspect of the present disclosure includes an imaging unit that generates image data by capturing an image of a tooth inside the mouth of a user, an orientation detector that detects the orientation of the imaging unit according to output by a multi-axis acceleration sensor, an area detector that detects, according to the orientation detected, an area whose image is being captured by the imaging unit from among areas inside the mouth, the areas being determined by dividing a dentition into sections, and an identifier that narrows candidates which are combinations of tooth types and tooth positions down to fewer candidates to be used, according to the image data and the area detected, and identifies the type and position of the tooth according to the fewer candidates narrowed down and the image data.

Thus, the intraoral camera system detects the target area for image capturing, according to the orientation of the imaging unit and identifies the type and position of the tooth by using the detected area. Accordingly, it is possible to reduce the amount of processing and improve the accuracy of identification.

For instance, when detecting the area, the area detector may detect at least whether the area is a maxillary area or a mandibular area.

For instance, the areas may include areas included in the maxillary area and areas included in the mandibular area.

Since the intraoral camera system can divide the intraoral area into more specific areas, it is possible to improve the accuracy of identification.

For instance, the area detector may further detect the imaging direction according to the orientation detected, and the identifier may identify the type and the position of the tooth according to the image data, the area detected, and the imaging direction detected.

Since the intraoral camera system can divide the intraoral area into more specific areas, it is possible to improve the accuracy of identification.

For instance, the identifier may calculate evaluation values for the candidates which are the combinations of tooth types and tooth positions, by using the image data, correct the evaluation values according to the area detected, and identify, by using the evaluation values corrected, the type and the position of the tooth shown in the image data.

For instance, the identifier may identify the type and the position of the tooth by using an estimation model that includes a neural network and outputs the type and the position of the tooth when the image data and the area detected are input to the estimation model.

For instance, the identifier may detect interdental positions from the image data, generate tooth images each showing a tooth, according to the interdental positions detected, and identify the type and position of the tooth shown in each of the tooth images, according to the tooth images and the area detected.

For instance, the intraoral camera system may further include a user information obtainer that obtains user information indicating at least one of the gender, age group, and race of the user. The identifier may identify the type and the position of the tooth according to the user information, the image data, and the area detected.

Since the intraoral camera system can perform appropriate identification according to, for example, the user information, it is possible to improve the accuracy of identification.

For instance, the intraoral camera system may obtain an initial orientation which is a predetermined orientation of the imaging unit, and the area detector may adjust, by using the initial orientation, the orientation detected and detect, according to the orientation adjusted, the area whose image is being captured by the imaging unit from among the areas.

Thus, the intraoral camera system can improve the accuracy of processing by adjusting the orientation of the imaging unit according to the posture of the user.

For instance, the predetermined orientation may be the orientation of the imaging unit when the posture of the user and the orientation of the imaging unit have a predetermined relationship.

For instance, the imaging unit may include a handle, a head, and a neck, the head including an image sensor that generates image data, the neck connecting the handle to the head, and in the predetermined orientation, the imaging plane of the imaging unit may be parallel to the frontal plane of the user, and the vertical axis of the user and the direction from the handle toward the head may be identical or orthogonal when viewed in the direction perpendicular to the imaging plane.

For instance, the imaging unit may include a handle, a head, and a neck, the head including an image sensor that generates image data, the neck connecting the handle to the head, and in the predetermined orientation, a predetermined tooth and the imaging plane of the imaging unit may be parallel to and face each other, and the direction from the handle toward the head and a height direction of the predetermined tooth may be identical or orthogonal when viewed in the direction perpendicular to the imaging plane.

Thus, the user can readily obtain the initial orientation. In addition, improvement of the accuracy of the initial orientation leads to improvement of the accuracy of adjustment.

In addition, a tooth identification method according to another aspect of the present disclosure includes generating image data by an imaging unit capturing an image of a tooth inside the mouth of a user, detecting the orientation of the imaging unit according to output by a multi-axis acceleration sensor and detecting, according to the orientation detected, an area whose image is being captured by the imaging unit from among areas inside the mouth, the areas being determined by dividing a dentition into sections, and narrowing candidates which are combinations of tooth types and tooth positions down to fewer candidates to be used, according to the image data and the area detected, and identifying the type and position of the tooth shown in the image data, according to the fewer candidates narrowed down and the image data.

Thus, in the tooth identification method, the target area for image capturing is detected according to the orientation of the imaging unit, and the type and position of the tooth are detected using the detected area. Accordingly, it is possible to reduce the amount of processing and improve the accuracy of identification.

It should be noted that these general or specific aspects may be embodied as a system, a method, an integrated circuit, a computer program, or a computer-readable recording medium, such as a CD-ROM, or may be embodied by any combination of the system, the method, the integrated circuit, the computer program, and the recording medium.

An embodiment is described below in detail with reference to the drawings as necessary. However, excessively detailed explanations may be omitted. For instance, detailed explanations for well-known matters and overlapping explanations for substantially the same structural elements may be omitted. Such an omission is made to avoid unnecessary redundancy of the descriptions below and to facilitate understanding by those skilled in the art.

It should be noted that the inventors of the present disclosure provide the appended drawings and the following descriptions for thorough understanding of the present disclosure by those skilled in the art. There is no intention to limit the present disclosure by the appended drawings and the following descriptions.

Embodiment

FIG. 1 is a perspective view of the intraoral camera of an intraoral camera system according to the embodiment. As illustrated in FIG. 1, intraoral camera 10 includes a toothbrush-shaped case that can be handled by one hand. The case includes head 10a, handle 10b, and neck 10c. Head 10a is put inside a user's mouth when a dentition image is captured. Handle 10b is designed to be held by a user. Neck 10c connects head 10a to handle 10b.

Imaging optical system 12 is incorporated into head 10a and neck 10c. Imaging optical system 12 includes image sensor 14 and a lens (not illustrated in FIG. 1) disposed on optical axis LA.

Image sensor 14 is an image device, such as a C-MOS sensor or a CCD sensor, and the lens forms an image of a tooth. Image sensor 14 outputs a signal (image data) corresponding to the formed image to an external device.

In addition, intraoral camera 10 is equipped with first to fourth LEDs 26A to 26D as lighting devices that illuminate a target tooth during image capturing. First to fourth LEDs 26A to 26D are, for example, white LEDs.

Figure 2:
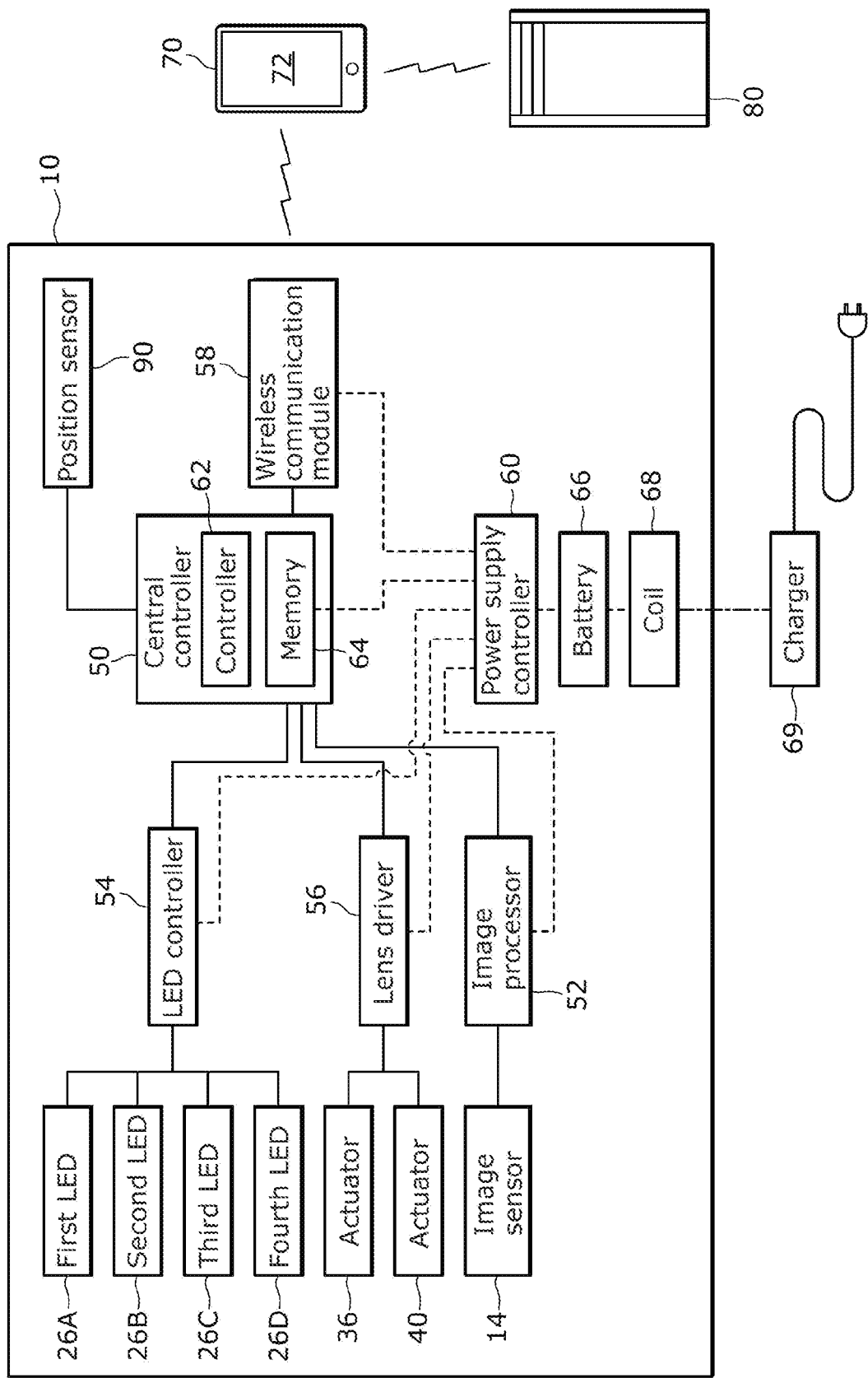
FIG. 2 illustrates a schematic configuration of the intraoral camera system according to the embodiment.

FIG. 2 is a schematic configuration of the intraoral camera system according to the embodiment. As illustrated in FIG. 2, in the overview of operation, the intraoral camera system according to the embodiment captures a dentition image by using intraoral camera 10 and performs image processing for the captured image.

As illustrated in FIG. 2, the intraoral camera system includes intraoral camera 10, portable terminal 70, and cloud server 80. Portable terminal 70 is, for example, a wirelessly communicable smartphone or a tablet terminal. Portable terminal 70 includes, as an input device and an output device, touch screen 72 capable of displaying, for example, a dentition image. Portable terminal 70 functions as a user interface of the intraoral camera system.

Cloud server 80 can communicate with portable terminal via, for example, the Internet and provides portable terminal with an application to use intraoral camera 10. For instance, the user downloads the application from cloud server 80 and installs the application on portable terminal 70. In addition, cloud server 80 obtains a dentition image captured by intraoral camera 10 via portable terminal 70.

The intraoral camera system includes, as main elements that controls the system, central controller 50, image processor 52, LED controller 54, lens driver 56, and position sensor 90. Image processor 52 performs image processing for a dentition image captured by image sensor 14. LED controller 54 controls LEDs 26A to 26D. Lens driver 56 controls actuator 36 that is a composition adjustment mechanism and actuator 40 that is a focus adjustment mechanism.

In addition, the intraoral camera system includes wireless communication module 58 that wirelessly communicates with portable terminal 70 and power supply controller 60 that supplies power to, for example, central controller 50.

Central controller 50 of the intraoral camera system is incorporated into, for example, handle 10b of intraoral camera 10. For instance, central controller 50 includes controller 62, such as a CPU or an MPU, that performs various processing tasks described later and memory 64, such as RAM or ROM, storing programs used to cause controller 62 to perform the various processing tasks. It should be noted that in addition to the programs, dentition images captured by image sensor 14 (image data) and various setting data items are stored in memory 64.

Image processor 52 is incorporated into, for example, handle 10b of intraoral camera 10. On the basis of a control signal from controller 62 of central controller 50, image processor 52 obtains a dentition image captured by image sensor 14 (image data), performs the image processing for the obtained dentition image, and outputs, to central controller 50, the dentition image that has undergone the image processing. Image processor 52 is, for example, a circuit and performs, for the dentition image, the image processing such as noise removal and automatic white balance (AWB) adjustment. Controller 62 transmits the dentition image output by image processor 52 to portable terminal 70 via wireless communication module 58. Portable terminal 70 displays the transmitted dentition image on touch screen 72. In this way, touch screen 72 displays the dentition image to the user.

LED controller 54 is incorporated into, for example, handle of intraoral camera 10 and turns on and off first to fourth LEDs 26A to 26D on the basis of a control signal from controller 62. LED controller 54 is, for example, a circuit. When for instance the user performs an operation to start intraoral camera for touch screen 72 of portable terminal 70, portable terminal transmits a signal corresponding to the operation to controller 62 via wireless communication module 58. On the basis of the received signal, controller 62 transmits the control signal to LED controller 54 to turn on first to fourth LEDs 26A to 26D.

Lens driver 56 is incorporated into, for example, handle of intraoral camera 10 and controls actuator 36, which is the composition adjustment mechanism, and actuator 40, which is the focus adjustment mechanism, on the basis of control signals from controller 62 of central controller 50. Lens driver 56 is, for example, a circuit. When for instance the user performs operations regarding composition adjustment and focus adjustment for touch screen 72 of portable terminal 70, portable terminal 70 transmits signals corresponding to the operations to central controller 50 via wireless communication module 58. On the basis of the received signals, controller 62 of central controller 50 transmits the control signals to lens driver 56 to perform composition adjustment and focus adjustment. In addition, for instance, on the basis of the dentition image received from image processor 52, controller 62 calculates the amount of control for actuator 36 necessary to perform composition adjustment and the amount of control for actuator necessary to perform focus adjustment. Then, control signals corresponding to the calculated amounts of control are transmitted to lens driver 56.

Wireless communication module 58 is incorporated into, for example, handle 10b of intraoral camera 10 and wirelessly communicates with portable terminal 70 on the basis of a control signal from controller 62. Wireless communication module 58 performs, with portable terminal 70, wireless communication that complies with an existing communication standard, such as Wi-Fi (registered trademark) or Bluetooth (registered trademark). Intraoral camera 10 transmits a dentition image showing tooth D to portable terminal 70 via wireless communication module 58, and portable terminal 70 transmits an operation signal to intraoral camera 10 via wireless communication module 58.

In the embodiment, power supply controller 60 is incorporated into handle 10b of intraoral camera 10 and distributes the power of battery 66 to central controller 50, image processor 52, LED controller 54, lens driver 56, and wireless communication module 58. Power supply controller 60 is, for example, a circuit. It should be noted that in the embodiment, battery 66 is a rechargeable battery (secondary battery), and external charger 69 connected to a commercial power supply wirelessly recharges battery 66 via coil 68 included in intraoral camera 10.

Position sensor 90 is used to detect the orientation and position of intraoral camera 10 and is, for example, a multi-axis (here, x, y, and z-axis, that is, three-axis) acceleration sensor. For instance, position sensor 90 may be a six-axis sensor including a three-axis acceleration sensor and a three-axis gyro sensor. For instance, as illustrated in FIG. 1, the z-axis is identical to optical axis LA. The y-axis is parallel to an imaging plane and extends in a longitudinal direction of intraoral camera 10. In addition, the x-axis is parallel to the imaging plane and orthogonal to the y-axis. Output (sensor data) for each axis of position sensor 90 is transmitted to portable terminal 70 via central controller 50 and wireless communication module 58.

A piezo-resistive type, capacitive type, or heat detection type MEMS sensor may be used as position sensor 90. Although not illustrated in the figure, it is preferable to provide a correction circuit for correcting, for example, the balance of sensor sensitivity between the axes, the temperature characteristics of sensitivity, and temperature drift. In addition, a bandpass filter (low pass filter) for removing dynamic acceleration components and a noise may be provided. A noise can be reduced also by smoothing a waveform output by the acceleration sensor.

Figure 3:
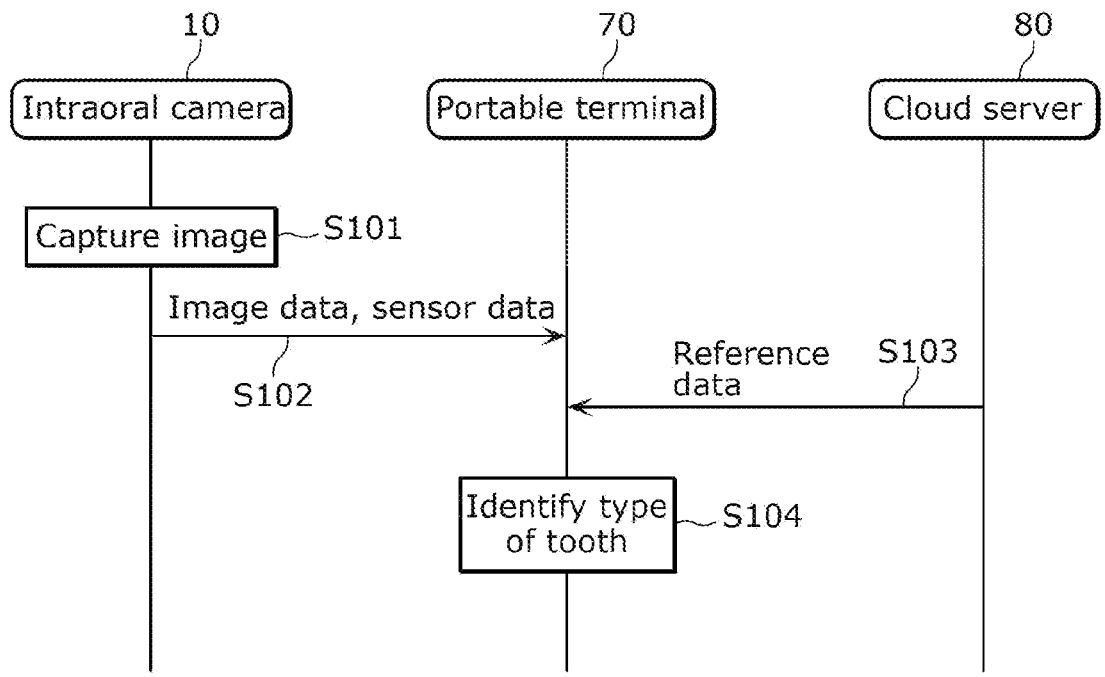
FIG. 3 illustrates a procedure of intraoral-image capturing operation of the intraoral camera system according to the embodiment.

Intraoral-image capturing operation of the intraoral camera system is described below. FIG. 3 illustrates a procedure of intraoral-image capturing operation of the intraoral camera system.

When the user captures an image of a tooth and gums inside their mouth by using intraoral camera 10, image data is generated (S101). Then, intraoral camera 10 transmits, to portable terminal 70, the captured image data and sensor data obtained by position sensor 90 during the image capturing (S102). It should be noted that the image data may be a video or one or more still images. In addition, if the image data is a video or includes two or more still images, the sensor data is transmitted for each video frame or for each still image. It should be noted that if the image data is a video, the sensor data may be transmitted every two or more frames.

In addition, the image data and the sensor data may be transmitted in real time or together after a series of image capturing (for example, images of all the teeth inside the user's mouth are captured).

Portable terminal 70 obtains reference data from cloud server 80 (S103) and identifies the types and positions of teeth included in image data items by using the received image data items and sensor data and the obtained reference data (S104).

Figure 4:
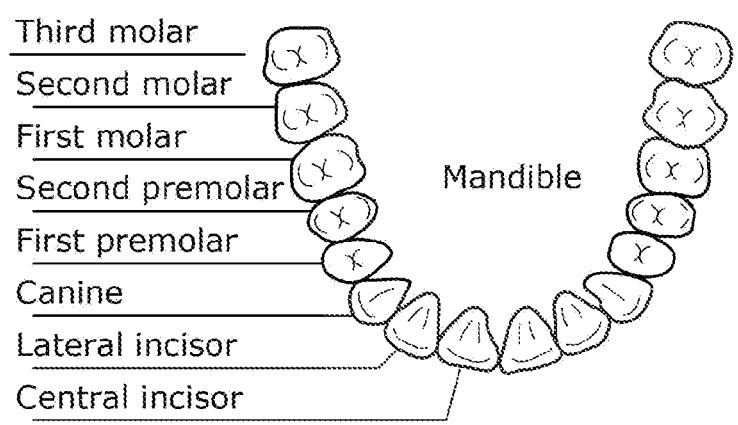
FIG. 4 illustrates teeth inside a mouth according to the embodiment.

FIG. 4 illustrates teeth inside a mouth. The types of teeth identified by portable terminal 70 are, for example, the central incisors, the lateral incisors, and the canines illustrated in FIG. 4. The positions of teeth identified by portable terminal 70 correspond to, for example, the maxilla, the mandible, the right side, and the left side. That is, to identify the type and position of a tooth is to identify the target tooth from the teeth illustrated in FIG. 4.

In addition, for instance, portable terminal 70 may generate a three-dimensional model of the teeth inside the user's mouth from the captured image data items, by using the identified types and positions of the teeth, and display an image based on the generated three-dimensional model.

By using such an intraoral camera system, the user can capture, by intraoral camera 10, an intraoral image showing the interior of their mouth and check their intraoral condition displayed on portable terminal 70. Thus, the user can readily check the health condition of their teeth, for instance.

It should be noted that in the example below, portable terminal 70 identifies, for example, the types of teeth. However, a part or all of the processing performed by portable terminal 70 may be performed by intraoral camera 10 or cloud server 80.

Figure 5:
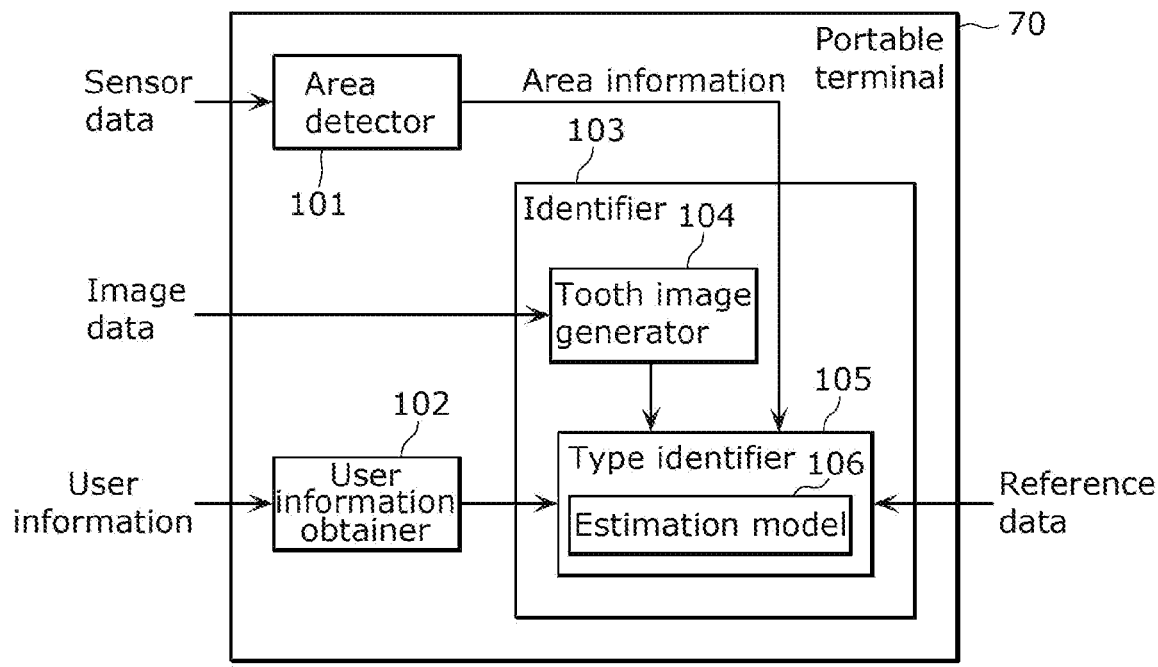
FIG. 5 is a functional block diagram of a portable terminal according to the embodiment.

FIG. 5 is a functional block diagram of portable terminal Portable terminal 70 includes area detector 101, user information obtainer 102, and identifier 103. The functions of these processing units are achieved, for example, by a program executer, such as a CPU or a processor, reading and executing a software program stored in a recording medium, such as a hard disk or semiconductor memory.

Area detector 101 detects intraoral areas corresponding to respective image data items by using the sensor data and generates area information items indicating the respective detected areas.

User information obtainer 102 obtains user information indicating a user attribute. For instance, user information obtainer 102 obtains user information input by the user via a user interface of portable terminal 70. Alternatively, user information obtainer 102 may obtain user information stored in portable terminal 70 or another device (e.g., cloud server 80). Specifically, the user information indicates at least one of the gender, age group (or age), and race of the user.

Identifier 103 identifies the types and positions of the teeth included in the image data items by using the image data items, the area information items, the user information, and the reference data. Identifier 103 includes tooth image generator 104 and type identifier 105. Tooth image generator 104 generates, from the image data items, tooth images each showing a tooth. Type identifier 105 identifies the type and position of a tooth included in a tooth image by using an area information item, the user information, the reference data, and estimation model 106.

Estimation model 106 is a model for estimating the type and position of a tooth included in a tooth image from the tooth image and the reference data. For instance, estimation model 106 may include a neural network.

Figure 6:
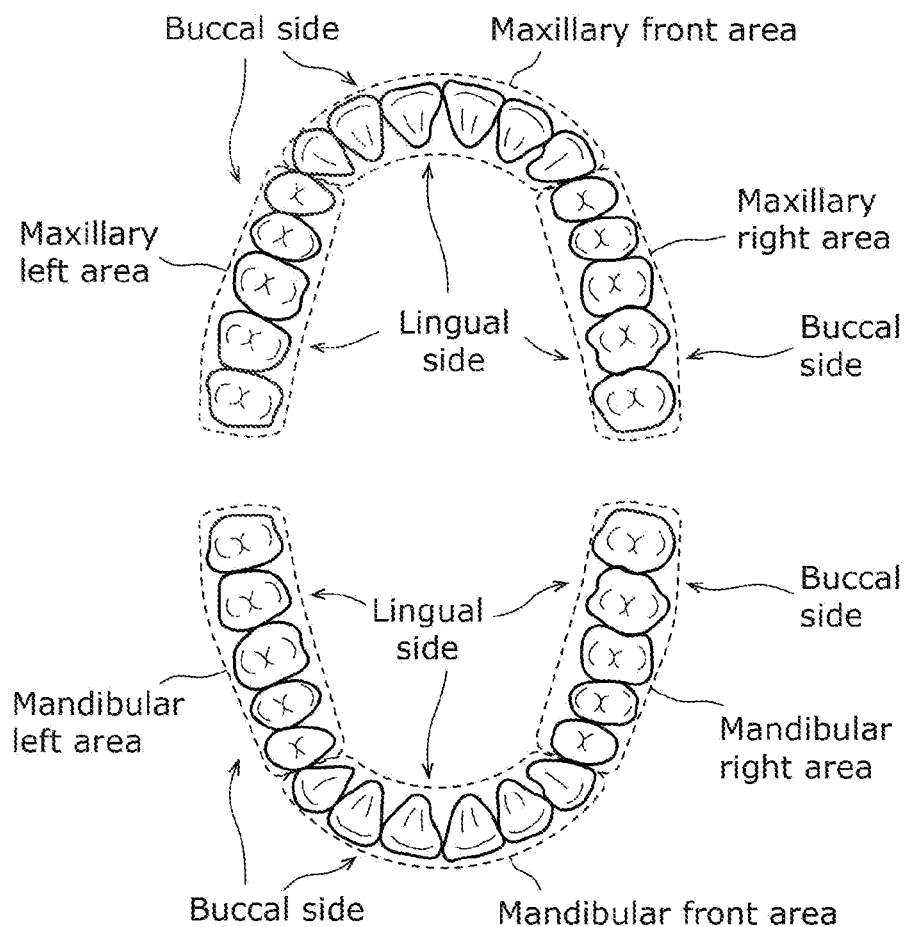
FIG. 6 illustrates an example of intraoral areas according to the embodiment.

An example of areas detected by area detector 101 is described below. FIG. 6 illustrates an example of intraoral areas. In FIG. 6, for instance, each tooth inside the mouth belongs to one of six areas: the maxillary left area, the maxillary front area, the maxillary right area, the mandibular left area, the mandibular front area, and the mandibular right area. It should be noted that the intraoral area is divided into six areas in the example. However, the number of areas may be any number. For instance, the intraoral area may be divided into two areas: a maxillary area and a mandibular area. In addition, each area may further be divided on the basis of imaging directions. For instance, as illustrated in FIG. 6, each area may be divided into a buccal-side area and a lingual-side area on the basis of two imaging directions. In the example, each tooth does not belong to more than one area. However, some of the teeth may belong to two or more areas. For instance, a tooth near the boundary of two adjacent areas may belong to both areas. For instance, in FIG. 6 the canine at the left end of the maxillary front area, which is the third tooth in the palmer notation method, may belong to both of the maxillary front area and the maxillary left area.

A specific example of a method of determining the area and the imaging direction from the sensor data is described below. Area detector 101 determines whether the area is maxillary or mandibular according to output Az by the acceleration sensor for the z-direction. Here, when a maxillary-dentition image is captured, an imaging plane faces upward to no small extent. When a mandibular-dentition image is captured, the imaging plane faces downward to no small extent. Thus, when $Az>0$, area detector 101 determines that the area corresponding to the image data is mandibular. When $Az \leq 0$, area detector 101 determines that the area corresponding to the image data is maxillary.

Then, a method of determining which area of the maxilla the area is, which is performed when it is determined that the area is maxillary, is described below. Area detector 101 determines whether the tooth is an anterior tooth, according to output Ay by the acceleration sensor for the y-direction. Here, when an image of an anterior tooth is captured, intraoral camera is relatively horizontal. However, when an image of a molar is captured, intraoral camera 10 has to be tilted due to interference of lips. Thus, when Ay≤threshold a, area detector 101 determines that the area is the maxillary front area.

After determining that the area is the maxillary front area, area detector 101 further determines whether the area is the buccal-side area or the lingual-side area, according to output Ax by the acceleration sensor for the x-direction. Here, the orientation of the imaging plane when an image of the buccal side of a tooth is captured is opposite to the orientation of the imaging plane when an image of the lingual side of a tooth is captured. Thus, when Ax>0, area detector 101 determines that the area is the maxillary front buccal-side area. When Ax≤0, area detector 101 determines that the area is the maxillary front lingual-side area.

Meanwhile, when determining that the area is not the maxillary front area, area detector 101 determines the orientation of the imaging plane according to output Ax by the acceleration sensor for the x-direction. Specifically, when Ax>0, area detector 101 determines that the area is the maxillary right buccal-side area or the maxillary left lingual-side area. When Ax≤0, area detector 101 determines that the area is the maxillary left buccal-side area or the maxillary right lingual-side area.

Area detector 101 further narrows down the areas according to the area determined in the previous processing. Specifically, when area detector 101 determines whether the area is the maxillary right buccal-side area or the maxillary left lingual-side area, if the previously determined area is one of the maxillary front buccal-side area, the maxillary right buccal-side area, the maxillary right lingual-side area, the mandibular front buccal-side area, the mandibular right buccal-side area, and the mandibular right lingual-side area, area detector 101 estimates that the current area is the maxillary right buccal-side area. If the previously determined area is one of the maxillary front lingual-side area, the maxillary left buccal-side area, the maxillary left lingual-side area, the mandibular front lingual-side area, the mandibular left buccal-side area, and the mandibular left lingual-side area, area detector 101 estimates that the current area is the maxillary left lingual-side area.

When area detector 101 determines whether the area is the maxillary left buccal-side area or the maxillary right lingual-side area, if the previously determined area is one of the maxillary front buccal-side area, the maxillary left buccal-side area, the maxillary left lingual-side area, the mandibular front buccal-side area, the mandibular left buccal-side area, and the mandibular left lingual-side area, area detector 101 estimates that the current area is the maxillary left buccal-side area. If the previously determined area is one of the maxillary front lingual-side area, the maxillary right buccal-side area, the maxillary right lingual-side area, the mandibular front lingual-side area, the mandibular right buccal-side area, and the mandibular right lingual-side area, area detector 101 estimates that the current area is the maxillary right lingual-side area. The estimation is based on a high probability of the imaging plane being moved to keep the amount of the movement of the imaging plane and the orientation change of the imaging plane to a minimum.

In addition, similar determination is performed for the mandible. Specifically, area detector 101 determines whether the tooth is an anterior tooth, according to output Ay by the acceleration sensor for the y-direction. Specifically, when Ay≤threshold b, area detector 101 determines that the area is the mandibular front area.

After determining that the area is the mandibular front area, area detector 101 further determines whether the area is the buccal-side area or the lingual-side area, according to output Ax by the acceleration sensor for the x-direction. Specifically, when Ax<0, area detector 101 determines that the area is the mandibular front buccal-side area. When Ax≥0, area detector 101 determines that the area is the mandibular front lingual-side area.

Meanwhile, when the area is not the mandibular front area, area detector 101 determines the orientation of the imaging plane according to output Ax by the acceleration sensor for the x-direction. Specifically, when Ax>0, area detector 101 determines that the area is the mandibular right buccal-side area or the mandibular left lingual-side area. When Ax≤0, area detector 101 determines that the area is the mandibular left buccal-side area or the mandibular right lingual-side area.

When area detector 101 determines whether the area is the mandibular right buccal-side area or the mandibular left lingual-side area, if the previously determined area is one of the mandibular front buccal-side area, the mandibular right buccal-side area, the mandibular right lingual-side area, the maxillary front buccal-side area, the maxillary right buccal-side area, and the maxillary right lingual-side area, area detector 101 estimates that the current area is the mandibular right buccal-side area. If the previously determined area is one of the mandibular front lingual-side area, the mandibular left buccal-side area, the mandibular left lingual-side area, the maxillary front lingual-side area, the maxillary left buccal-side area, and the maxillary left lingual-side area, area detector 101 estimates that the current area is the mandibular left lingual-side area.

When area detector 101 determines whether the area is the mandibular left buccal-side area or the mandibular right lingual-side area, if the previously determined area is one of the mandibular front buccal-side area, the mandibular left buccal-side area, the mandibular left lingual-side area, the maxillary front buccal-side area, the maxillary left buccal-side area, and the maxillary left lingual-side area, area detector 101 estimates that the current area is the mandibular left buccal-side area. If the previously determined area is one of the mandibular front lingual-side area, the mandibular right buccal-side area, the mandibular right lingual-side area, the maxillary front lingual-side area, the maxillary right buccal-side area, and the maxillary right lingual-side area, area detector 101 estimates that the current area is the mandibular right lingual-side area.

In the above processing, one of the maxillary front buccal-side area, the maxillary front lingual-side area, the maxillary right buccal-side area, the maxillary left lingual-side area, the maxillary left buccal-side area, the maxillary right lingual-side area, the mandibular front buccal-side area, the mandibular front lingual-side area, the mandibular right buccal-side area, the mandibular left lingual-side area, the mandibular left buccal-side area, and the mandibular right lingual-side area is determined as the current area.

It should be noted that the above determination algorithm is just an example, and any determination algorithm may be used as long as it is possible to identify the area from output Ax, output Ay, and output Az by the acceleration sensor. For instance, rather than using the values of output Ax, output Ay, and output Az as variables, a secondary variable obtained by appropriately combining output Ax, output Ay, and output Az may be used for the determination. The secondary variable can optionally be set to, for example, Ay/Az, Ax·AX+Ay·Ay, and Az−Ax. Alternatively, the area may be determined after acceleration information items for the axes, Ax, Ay, and Az are converted into angle information items (orientation angles) α, β, and γ. For instance, the angle of the x-axis relative to the direction of gravity acceleration may be defined as roll angle α, the angle of the y-axis relative to the direction of gravity acceleration may be defined as pitch angle β, and the angle of the z-axis relative to the direction of gravity acceleration may be defined as yaw angle γ. In addition, the threshold used in each determination can be determined from the results of, for example, clinical tests.

In addition, in the above example, the imaging direction is determined from the two imaging directions: the imaging direction when an image of the buccal side of a tooth is captured and the imaging direction when an image of the lingual side of the tooth is captured. However, the imaging direction may be determined from three imaging directions including the imaging direction when an image of the top of a tooth is captured. For instance, it is possible to determine whether the imaging direction is the direction when an image of the top of a tooth is captured, on the basis of the fact that the imaging plane is more horizontal when an image of the top of a tooth is captured, compared with when an image of the buccal side is captured and when an image of the lingual side is captured.

In addition, in the above example, the target area for image capturing of imaging unit 21 and the imaging direction of imaging unit 21 are determined using the three-axis acceleration sensor of position sensor 90. However, the target area for the image capturing and the imaging direction may be determined using a three-axis gyro sensor. The three-axis gyro sensor, for example, outputs the amount of angle change because of movement around the x-axis, the amount of angle change because of movement around the y-axis, and the amount of angle change because of movement around the z-axis. That is, for the three-axis gyro sensor, the amount of change for each axis is added under the condition that the initial states of the x-axis, the y-axis, and the z-axis are set to given states. Then, the target area for the image capturing and the orientation of the imaging plane of intraoral camera 10 (imaging direction) are determined.

It should be noted that the target area for the image capturing and the orientation of the imaging plane of intraoral camera 10 may be determined by combining the three-axis acceleration sensor and the three-axis gyro sensor.

Operation of identifier 103 is described below in detail. It should be noted that processing for an image data item (one frame included in a dynamic image or one still image) is described below.

First, tooth image generator 104 generates, from at least one image data item, tooth images each showing a tooth. Specifically, tooth image generator 104 detects interdental positions from the image data items by performing, for example, image analysis and extracts tooth images by using the detected interdental positions. For instance, tooth image generator 104 generates a tooth image by extracting an image by using an interdental position as a boundary.

Next, type identifier 105 identifies the type and position of a tooth included in each tooth image by using area information, user information, reference data, and estimation model 106.

The reference data is referenced when the type and position of the tooth included in the tooth image are identified. For instance, the reference data is tooth data in which the type and the position of each tooth are already known. Specifically, the reference data may be a group of pre-captured tooth image data items, a group of dentition image data items, or a panoramic dentition image. Alternatively, the reference data may be information indicating the standard shape of each tooth or the standard amount of features of each tooth.

It should be noted that reference data items may be classified not only by the type and the position, but also for each imaging direction and for each user attribute. It should be noted that the user attribute is one of the gender, age group (or age), and race of the user or a combination of at least two of the gender, the age group (or age), and the race. That is, the user attribute is uniquely determined by the gender, age group, and race of the user.

Figures 7, 8:
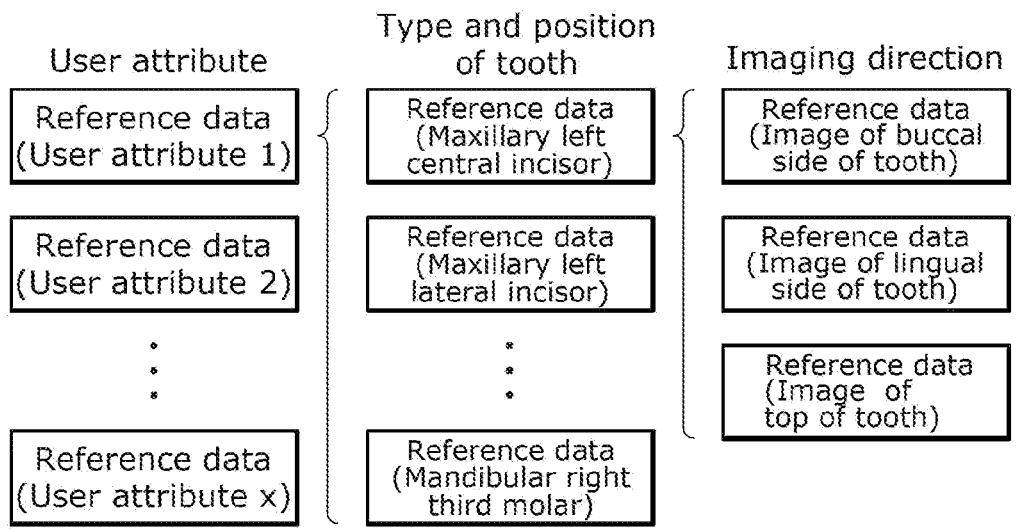
FIG. 7 illustrates an example of classification of reference data items according to the embodiment.
FIG. 8 illustrates examples of reference data items according to the embodiment.

FIG. 7 illustrates an example of classification of reference data items. It should be noted that although FIG. 7 illustrates hierarchical classification of the reference data items, the reference data items do not necessarily have to be hierarchically classified. In addition, reference data items used for identification are expressed as A(n). Furthermore, n is uniquely associated with a set of the type and position of a tooth and an imaging direction. FIG. 8 illustrates examples of the reference data items. As an example, FIG. 8 illustrates reference data items regarding the buccal side, the lingual side, and the top of each of a maxillary incisor, a maxillary canine, and a maxillary first molar.

As illustrated in FIG. 8, the shape and size of a tooth is different by the type of the tooth. For example, the maxillary central incisors have the following features. The typical external shape of the buccal side of a maxillary central incisor is vertically long trapezoidal, and the incisal edge of the central incisor is almost straight. The cervical line is convex toward the tooth root, and the mesial margin and the distal margin of the tooth are slightly curved. The curvature apex of the mesial margin is at or near the mesio-incisal angle. The curvature apex of the distal margin is at the position equivalent to one third of the length of the distal margin in the direction from the incisal edge toward the gingiva. The external shape of lingual-side of the tooth is triangular, and the mesial and distal marginal ridges and the linguocervical ridge (cingulum) form a marginal ridge, which forms a lingual fossa.

In addition, the maxillary canines have the following features. The typical external shape of the buccal side of a maxillary canine is pentagonal, and the maxillary canine has an elevation in the center of the incisal edge, which forms a cusp tip. The cervical line is convex toward the tooth root. The mesial margin of the tooth is straight or is slightly outwardly convex, and the distal margin of the tooth is straight or is slightly concave. The external shape of lingual-side of the tooth is rhomboid, and the mesial and distal marginal ridges and the linguocervical ridge (cingulum) form a marginal ridge.

In addition, the maxillary first molars have the following features. The typical external shape of the buccal side of a maxillary first molar is trapezoidal, and the mesial margin and the distal margin of the tooth are almost straight. The cervical line is horizontal, and a center portion of the cervical line has a projection at the furcation. The mesial contact point is at the position equivalent to one third of the height of the occlusal surface. The distal contact point is at the position equivalent to half the height of the occlusal surface. The external shape of lingual-side of the tooth is trapezoidal, and the lingual surface groove longitudinally runs through substantially the center. The external shape of the top of the tooth is parallelogrammatic, and the bucco-lingual diameter is greater than the mesio-distal diameter.

The tooth image to be processed is expressed as B(m). Thus, tooth images of the teeth next to the tooth included in the tooth image to be processed are expressed as B(m−1) and B(m+1).

In addition, area information corresponding to tooth image (B(m)) to be processed, which has been detected by area detector 101, is expressed as C(m). For instance, an area information item is generated for each image data item. Thus, when one image data item includes two or more teeth and two or more tooth images are generated, the two or more tooth images are associated with the same area information item corresponding to the one image data item.

Figure 9:
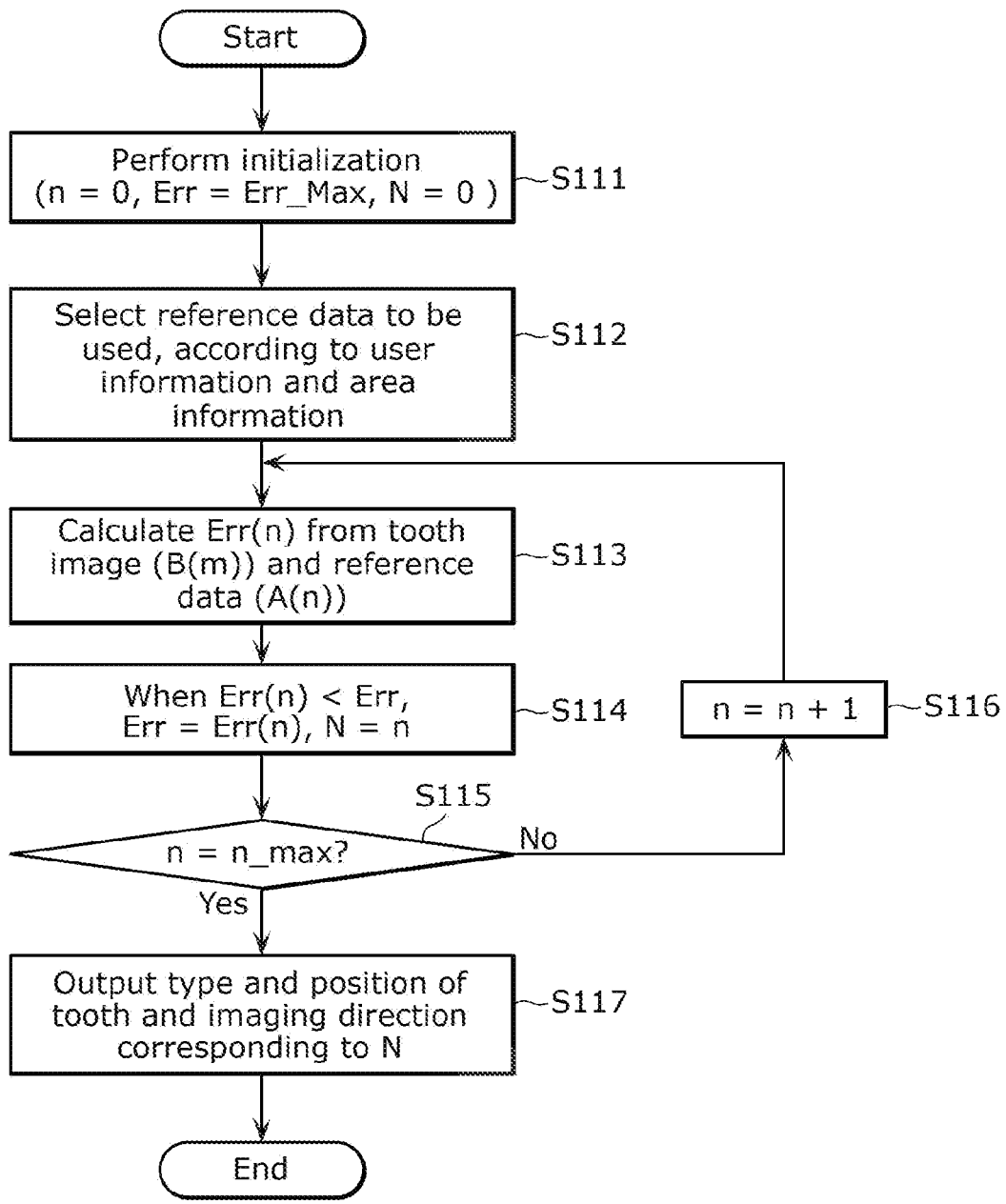
FIG. 9 is a flowchart illustrating type identification processing according to the embodiment.

FIG. 9 is a flowchart illustrating type identification processing performed by type identifier 105. First, type identifier 105 performs initialization (S111). Specifically, type identifier 105 sets n to 0, Err to Err_Max, and N to 0. Here, Err is an evaluation value, which is described later, and the smaller the value of Err, the higher the evaluation. In addition, Err_Max is the theoretical maximum value of Err. Furthermore, N denotes the minimum value of n of Err.

Next, type identifier 105 selects reference data items to be used, according to user information and area information (S112). Specifically, type identifier 105 selects reference data items to which a user attribute indicated by the user information is assigned and the types and positions of teeth and the imaging direction corresponding to an area indicated by the area information are assigned. When for instance the area indicated by the area information is the maxillary left lingual-side area, a total of five reference data items regarding the lingual side of the five teeth included in the maxillary left area are selected as reference data items to be used. In addition, n_max, which is the maximum value of n, is set according to the number of selected reference data items. For instance, when the number of the reference data items is five, n=0 to 4 is assigned to the five reference data items, and n_max is set to 4.

Then, type identifier 105 calculates Err(n) from tooth image B(m) and reference data (A(n)) (S113). For instance, type identifier 105 calculates Err(n) by using Err(n)=f(A(n))−f(B(nn)). Here, f(A(n)) is a value when A(n) is put into function f( ) and f(B(m)) is a value when B(m) is put into function f( ) Function f( ) is a function to extract the amount of features of each of A(n) and B(m). It should be noted that f( ) may be expressed as a vector instead of a scalar.

As illustrated in FIG. 8, each tooth has a distinctive shape and size according to the type of the tooth. By using function f described above, type identifier 105 extracts the distinctive shape and size of each tooth as the amount of features.

Figure 10:
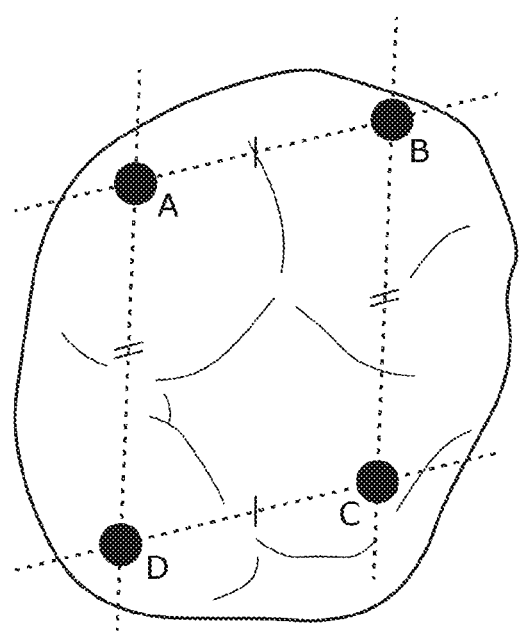
FIG. 10 illustrates an example of a tooth image according to the embodiment.

The amount of features extracted by using function f is described with reference to FIG. 10. FIG. 10 illustrates an image of the top of the maxillary right first molar. The occlusal surface of the first molar has a shape close to a parallelogram, and line AB connecting the mesial lingual cusp tip to the mesial buccal cusp tip is close to parallel to line DC connecting the distal lingual cusp tip to the distal buccal cusp tip. Line AD is close to parallel to line BC. In addition, the distances between the cusp tips are substantially equal (AB=DC, AD=BC). As an example, the above two distances between the cusp tips can be used as the amount of features.

In addition, Err(n) is a value denoting a difference (distance in the case of a vector) between f(A(n)) and f(B(m)). That is, the closer B(m) is to A(n), the smaller "f1(A(n))−f1(B(m))" is. When n=m, Err(n) has a local minimum value.

When calculated Err(n) is smaller than Err, type identifier 105 sets Err to Err(n) and N to n (S114).

When n≠n_max (No in S115), type identifier 105 increments n by 1 (S116) and performs step S113 and the subsequent steps again. That is, steps S113 and S114 are performed for all the reference data items used.

When n=n_max (Yes in S115), type identifier 105 outputs the type, the position, and the imaging direction corresponding to N, as the type, the position, and the imaging direction of a tooth included in the tooth image (S117).

Through the processing, type identifier 105 can identify the type, position, and imaging direction of the tooth included in the tooth image. In addition, in step S112, it is possible to narrow down candidates which are combinations of tooth types, tooth positions, and imaging directions, by using the user information and the area information. Thus, it is possible to reduce the amount of processing and improve the accuracy of identification.

Figure 11:
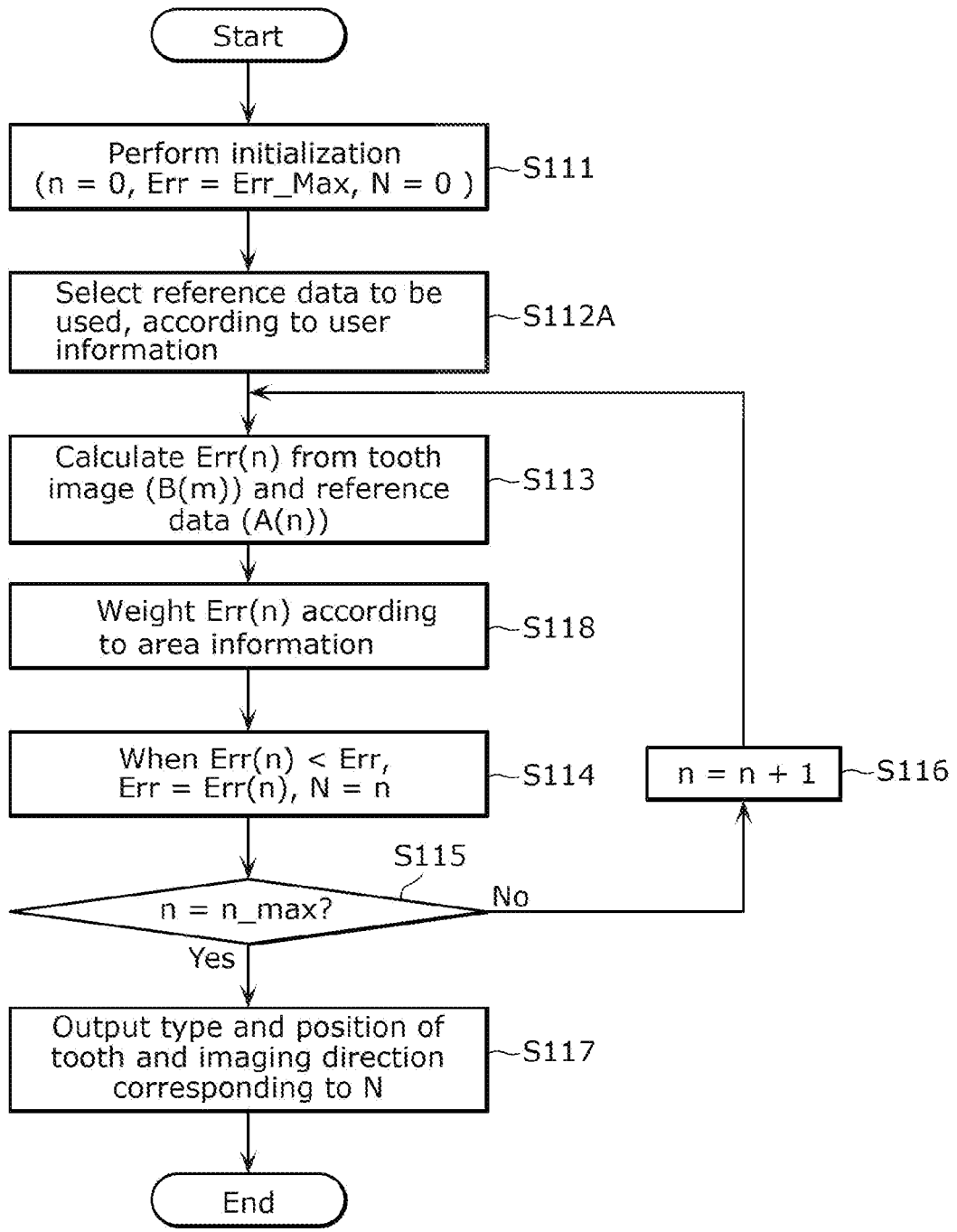
FIG. 11 is a flowchart illustrating another example of the type identification processing according to the embodiment.

FIG. 11 is a flowchart illustrating another example of the type identification processing performed by type identifier 105. In the processing illustrated in FIG. 11, step S112 illustrated in FIG. 9 is changed to step S112A, and step S118, which is not included in the processing illustrated in FIG. 9, is added.

In step S112A, type identifier 105 selects reference data items to be used, according to the user information. Specifically, type identifier 105 selects reference data items to which a user attribute indicated by the user information is assigned.

In step S118, type identifier 105 weights Err(n) calculated in step S113, according to the area information. Specifically, type identifier 105 multiplies Err(n) by w suitable for the area information. When for instance an area indicated by the area information includes the tooth corresponding to n, Err(n) is multiplied by w0. When for instance the area indicated by the area information does not include the tooth corresponding to n, Err(n) is multiplied by w1 greater than w0. This causes Err of the tooth included in the area indicated by the area information to be smaller, which increases the possibility of the tooth included in the tooth image being determined as the tooth included in the area.

In addition, weighting does not have to include two steps including the determination as to whether the area includes the tooth corresponding to n. For instance, weight may be set according to the distance from the area indicated by the area information. For instance, the weight of a tooth close to the area indicated by the area information may be set to be smaller than the weight of a tooth far from the area.

In addition, rather than using the user information for selecting reference data items, the user information may be used for weighting Err (n), as with the area information.

In addition, selection of reference data items according to the area information, as described with reference to FIG. 9 and weighting described with reference to FIG. 11 may be combined. For instance, a tooth far from the area indicated by the area information may be removed from the target, and weighting may be used for a tooth close to the area.

In addition, when tooth images of the user are obtained before, for example, in a case where the user regularly takes intraoral images, the tooth images may be used as reference data items. In this case, selection of reference data items according to the user information is not performed, and only the processing based on the area information is performed.

In addition, in the above example, a tooth image to be processed and reference data items are compared. However, two or more tooth images corresponding to a dentition including a tooth included in a tooth image to be processed and two or more reference data items may be compared.

For instance, type identifier 105 may calculate Err(n) by Err(n)=f(A(n))−f(B(m))+f'(A(n−1))−f'(B(m−1))+f'(A(n+1))−f'(B(m+1)). Here, A(n−1) and A(n+1) are reference data items on the teeth next to the tooth corresponding to A(n). B(m−1) and B(m+1) are the tooth images of the teeth next to the tooth corresponding to B(m). In addition, f'( ) is a function for extracting the amount of features to evaluate teeth on both side of a tooth of interest. It is possible to improve the accuracy of identification by using the information on the teeth next to the tooth of interest in this way.

In addition, in the above example, a tooth image is used as a reference data item. However, the amount of features (that is, the value of f(A(n))) may be used as a reference data item.

Estimation model 106 used for identification by type identifier 105 may include a learned model, such as a neural network. For instance, function f or function f', which is described above, may be the learned model. In addition, the method of using a neural network is not limited to the above example. For instance, whole estimation model 106, which estimates the type of a tooth, may be a neural network. In this case, for instance, estimation model 106 may be provided for each user attribute. Each estimation model 106 is a learned model generated by machine learning using, as training data items (learning data items), sets of a tooth image, area information, the type and position of a tooth, and the imaging direction for the user attribute corresponding to the estimation model. When a tooth image and area information are input to estimation model 106, estimation model 106 outputs the type and position of the tooth and the imaging direction. In this case, type identifier 105 selects corresponding estimation model 106 by using user information and inputs a tooth image and area information to selected estimation model 106 to obtain the type and position of a tooth and the imaging direction.

Alternatively, estimation model 106 may be provided for each set of user attribute and area information. In this case, each estimation model 106 is a learned model generated by machine learning using, as training data items, sets of a tooth image, area information, and the type and position of a tooth, and the imaging direction for the set of user attribute and area information corresponding to the estimation model. When a tooth image is input to estimation model 106, estimation model 106 outputs the type and position of a tooth and the imaging direction. In this case, type identifier 105 selects corresponding estimation model 106 by using user information and area information and inputs a tooth image to selected estimation model 106 to obtain the type and position of a tooth and the imaging direction.

It should be noted that in the example described above, both user information and area information are used. However, only one of the user information and the area information may be used.

In addition, in the example described above, area information indicates an area and an imaging direction. However, the area information may indicate only one of the area and the imaging direction.

Figure 12:
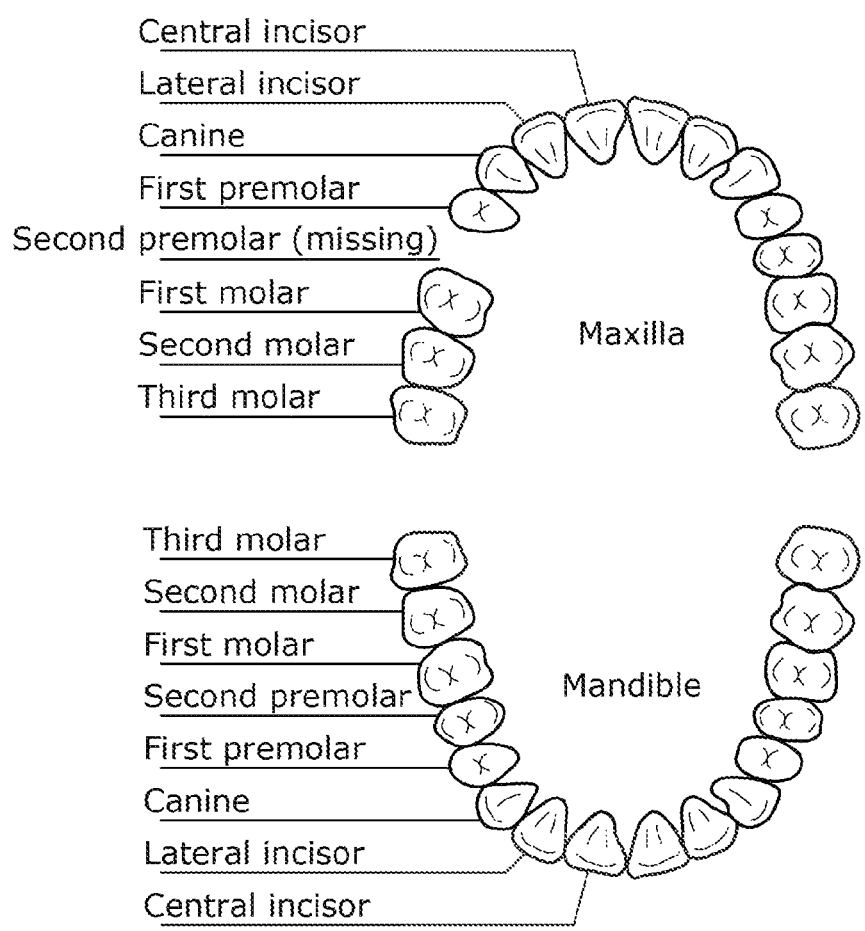
FIG. 12 illustrates a user's intraoral condition where a tooth is missing, according to the embodiment.

Operation of identifier 103 of the intraoral camera system performed when, for instance, a tooth (e.g., the maxillary left second premolar) of the user is missing because of treatment for a decayed tooth is described below in detail. It should be noted that processing for an image data item (one frame included in a dynamic image or one still image) is described below. FIG. 12 illustrates the user's intraoral condition where the maxillary left second premolar is missing.

Area detector 101 identifies that intraoral camera 10 is capturing an image of the maxillary left area including the second premolar. Then, intraoral camera 10 captures image B(m') of a portion corresponding to the second premolar and detects the non-existence of the tooth by, for example, image analysis.

Then, type identifier 105 calculates Err(n) from tooth image B(m'−1), tooth image B(m'+1), and reference data (A(n)), identifies the types and positions of teeth shown in tooth images B(m'−1) and B(m'+1), identifies that B(m') is an image of the area between the maxillary left first premolar and the maxillary left first molar, determines that the second premolar is missing, and outputs the result of the determination.

It should be noted that when the third molar is missing, it is possible to determine that the third molar is missing, by identifying the second molar next to the third molar.

In addition, when tooth images of the user are obtained before, for example, in a case where the user regularly takes intraoral images, the tooth images may be used as reference data items. In this case, it is possible to obtain information on the missing tooth of the user from the results of the previous intraoral-image capturing.

[Variation]

For instance, the above-mentioned determination of, for example, the tooth area and the imaging direction (generation of area information) based on the orientation of intraoral camera 10 is performed on the assumption that the user who is, for example, standing upright or sitting in a chair faces forward. Meanwhile, when, for example, a dentist captures an image of patient's teeth, the image may be captured in a state in which a user (patient) lies face upward. In such a case, the relationship between the vertical axis and the teeth differs from that in a state in which the user faces forward. Thus, determination may not be performed properly. Hereinafter, a method that enables proper determination even in such a case is described.

Figure 13:
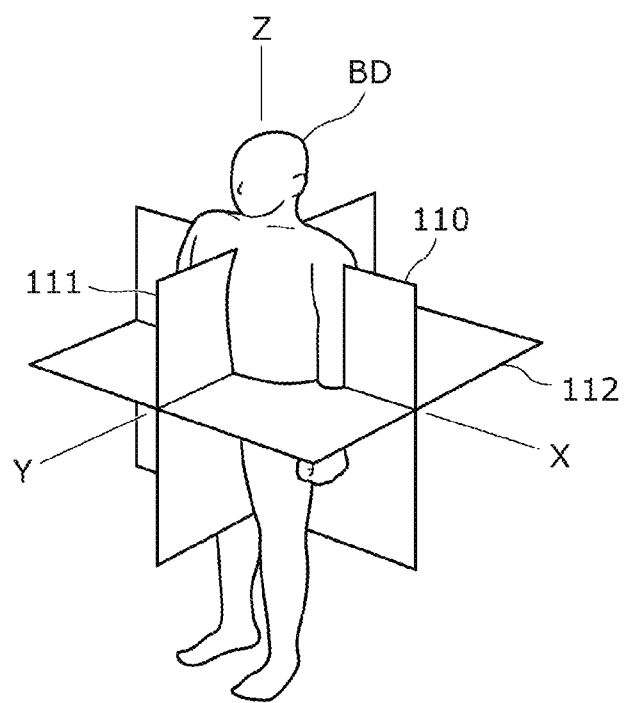
FIG. 13 illustrates relationships between projective planes and a standing user, according to a variation of the embodiment.

FIG. 13 illustrates relationships between projective planes and standing user BD. Here, the projective planes are virtual planes relative to user BD and include the three planes: frontal plane 110, sagittal plane 111, and transverse plane 112. Frontal plane 110 divides the body of user BD into anterior and posterior halves and is perpendicular to a floor surface. Sagittal plane 111 passes through the body of user BD from front to back and divides the body of user BD into right and left halves. Sagittal plane 111 is perpendicular to the floor surface. Transverse plane 112 is parallel to the floor surface and divides the body of user BD into superior (upper) and inferior (lower) halves. Transverse plane 112 is perpendicular to both frontal plane 110 and sagittal plane 111.

In addition, axes of motion are a vertical axis, a sagittal-transverse axis, and a frontal-transverse axis. The x-axis in FIG. 13 is the frontal-transverse axis. The sagittal-transverse axis is an axis in a left-right (horizontal) direction and the rotational axis of motions such as forward backward bend and flexion and extension on sagittal plane 111. The y-axis in FIG. 13 is the sagittal-transverse axis. The sagittal-transverse axis is an axis in an anteroposterior direction and is the rotational axis of motions such as side bend and abduction and adduction on frontal plane 110. The z-axis in FIG. 13 is the vertical axis. The vertical axis is an axis in a vertical direction and the rotational axis of motion such as rotational motion on transverse plane 112.

Figure 14:
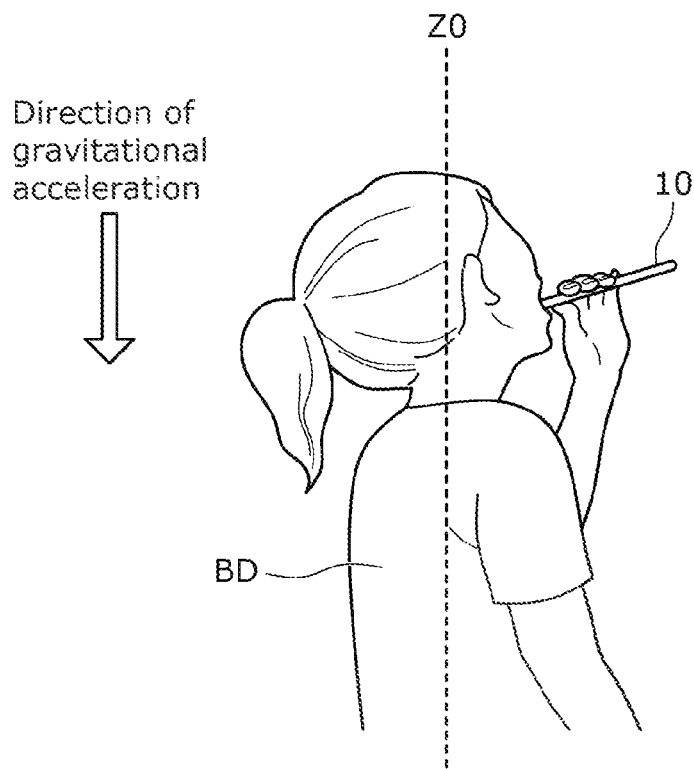
FIG. 14 illustrates an example of a user's posture during use of an intraoral camera, according to the variation of the embodiment.
Figure 15:
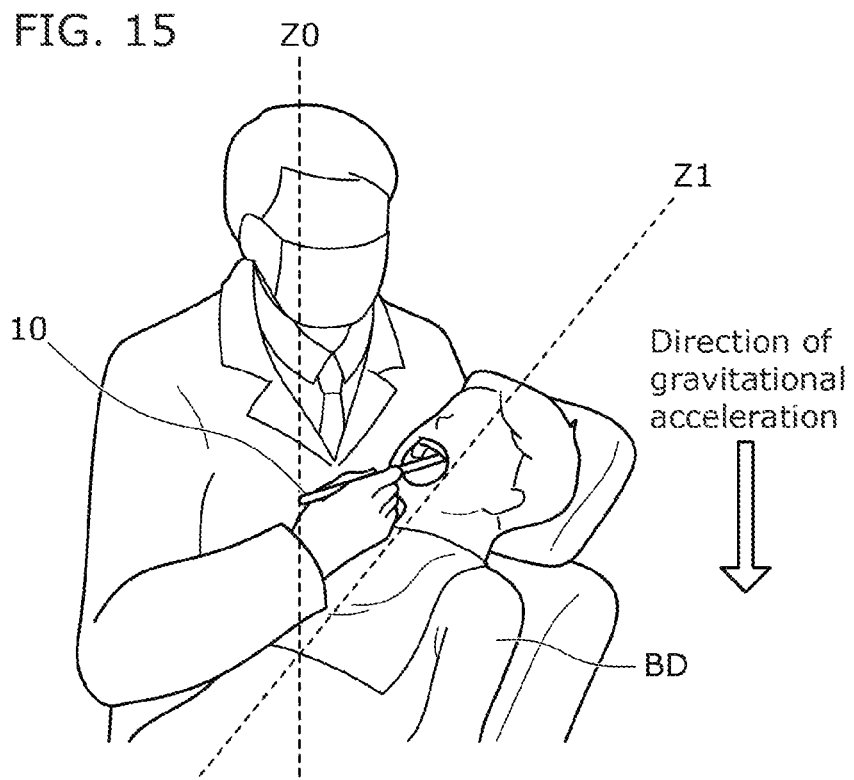
FIG. 15 illustrates an example of a user's posture during use of the intraoral camera, according to the variation of the embodiment.

FIGS. 14 and 15 each illustrate an example of the posture of user BD during use of intraoral camera 10.

As illustrated in FIG. 14, when user BD standing upright or sitting in a chair uses intraoral camera 10, it is possible to assume that the user is standing. At this time, vertical axis Z0 of the body of user BD (the z-axis) is perpendicular to the floor surface and identical to the direction in which gravitational acceleration acts.

Meanwhile, as illustrated in FIG. 15, when for instance a dentist uses intraoral camera 10 for user BD lying on a dental chair, frontal plane 110 of the upper body of user BD is tilted parallel to the back of the dental chair. That is, since frontal plane 110 of user BD is tilted, vertical axis Z1 of the user whose upper body is tilted parallel to the back of the dental chair tilts relative to vertical axis Z0 of the body of user BD standing upright.

Figure 16:
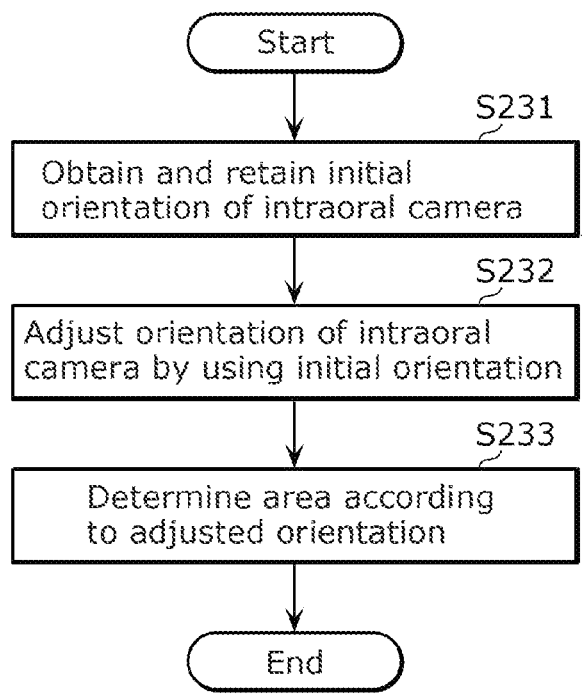
FIG. 16 is a flowchart illustrating image processing according to the variation of the embodiment.
Figure 17:
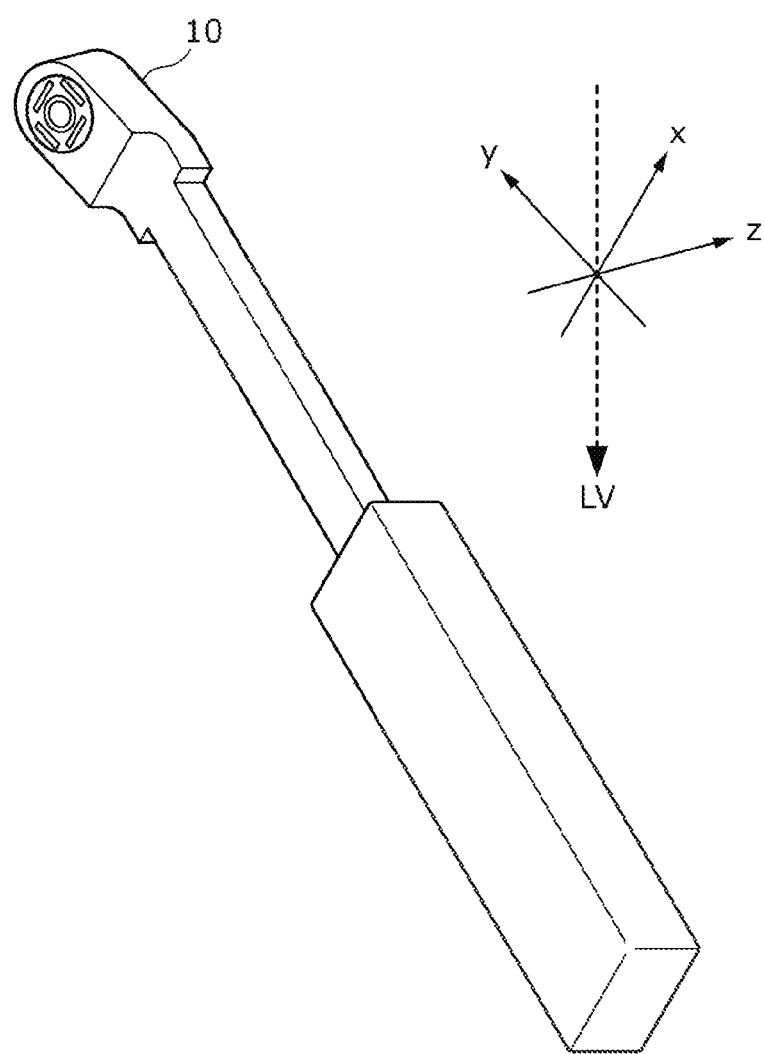
FIG. 17 illustrates an example of an initial orientation according to the variation of the embodiment.

FIG. 16 is a flowchart illustrating area detection processing performed by area detector 101 when the posture of user BD changes in this manner. First, area detector 101 obtains and retains the initial orientation of intraoral camera 10 (S231). Specifically, on the basis of a user operation, image processor 102 obtains, as the initial orientation, the orientation of intraoral camera 10 when the user operation was performed. For instance, the initial orientation is obtained on the basis of a user operation for portable terminal 70. Alternatively, the initial orientation is obtained when, for example, a button provided on intraoral camera 10 is pressed. FIG. 17 illustrates an example of the initial orientation. For instance, as illustrated in FIG. 17, orientation information on three axes relative to vertical direction LV, obtained by position sensor 90 that is a six-axis sensor is obtained as the initial orientation. Portable terminal or intraoral camera 10 retains the initial orientation.

Figure 18:
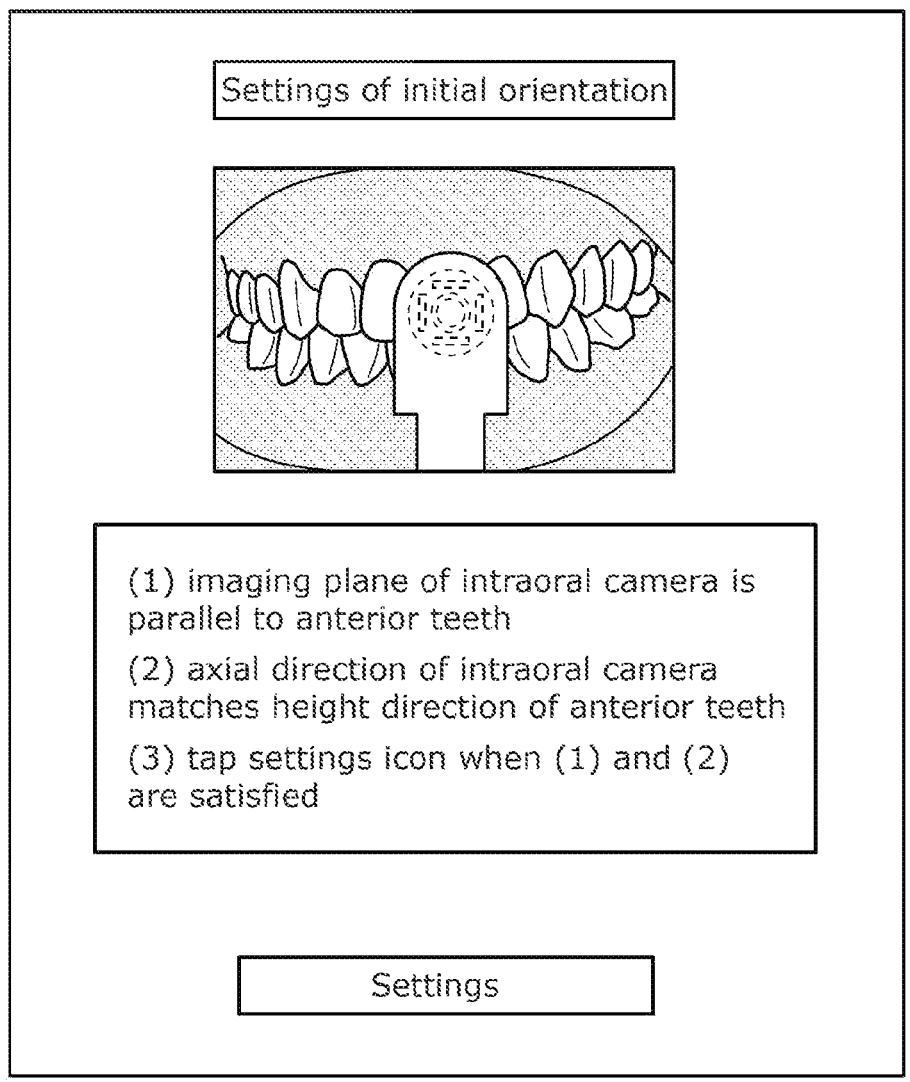
FIG. 18 illustrates an example of a setting screen to set the initial orientation according to the variation of the embodiment.

FIG. 18 illustrates an example of an initial-orientation setting screen on portable terminal 70. As illustrated in FIG. 18, for instance, the orientation of intraoral camera 10 when teeth and intraoral camera 10 have a predetermined relationship is obtained as the initial orientation. In the initial orientation described in the example illustrated in FIG. 18, imaging plane S of intraoral camera 10 is parallel to the front surfaces of anterior teeth, and the axial direction of intraoral camera 10 and a height direction of the anterior teeth are identical when viewed in the direction perpendicular to imaging plane S. Here, the axial direction is the direction from handle 10b toward head 10b, passing through the center of intraoral camera 10 in the longitudinal direction of intraoral camera 10. In addition, for instance, the axial direction is the direction passing through the center of imaging plane S in a vertical direction (column direction) of imaging plane S (image data).

It should be noted that a state in which the initial orientation is obtained is not limited to the above example and may be a given state based on at least one tooth. For instance, one or more teeth other than the anterior teeth may be used. In addition, part of the state specified above is the state in which the axial direction of intraoral camera 10 matches the height (longitudinal) direction of the anterior teeth. However, a state in which the axial direction of intraoral camera 10 is orthogonal to the height direction of the anterior teeth (a state in which the axis direction of intraoral camera 10 matches the width (lateral) direction of the anterior teeth) may be used.

In addition, the expressions: parallel, identical (match), and orthogonal described here are not limited to a perfectly parallel state, a perfectly identical state (perfect matching), and a perfectly orthogonal state. A substantially parallel state, a substantially identical state, and a substantially orthogonal state may be included. In other words, portable terminal 70 may instruct the user to achieve the above state, and the state used in the initial orientation may be the orientation of intraoral camera 10 achieved by the user in accordance with the instruction.

Figure 19:
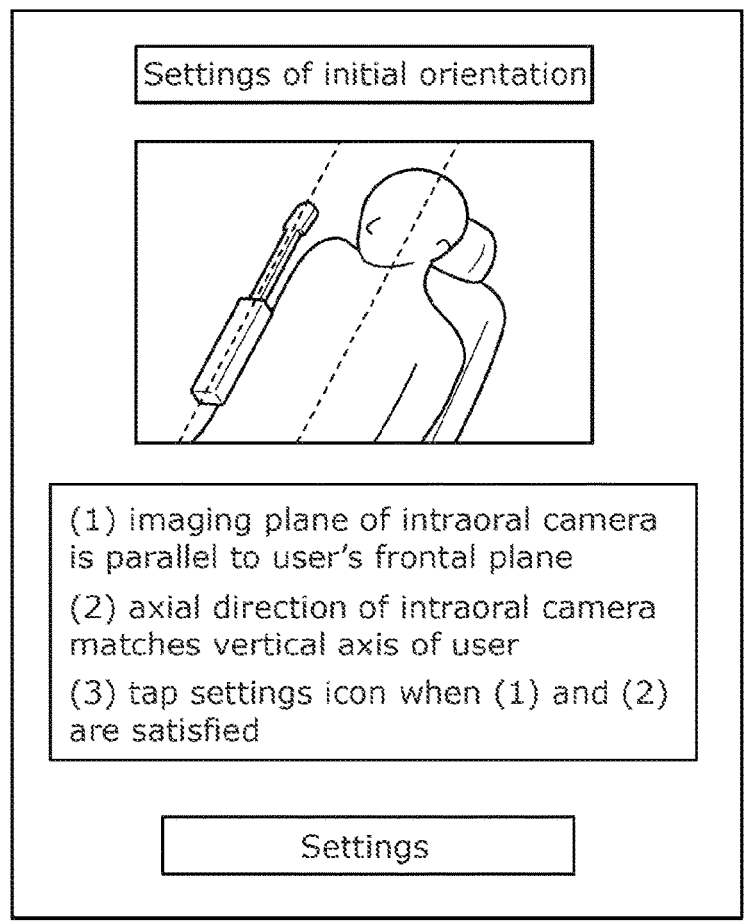
FIG. 19 illustrates an example of a setting screen to set the initial orientation according to the variation of the embodiment.

FIG. 19 illustrates another example of the initial-orientation setting screen on portable terminal 70. As illustrated in FIG. 19, for instance, the orientation of intraoral camera 10 when the posture of the user and the orientation of intraoral camera 10 have a predetermined relationship is obtained as the initial state. In the initial orientation described in the example illustrated in FIG. 19, imaging plane S of the imaging unit is parallel to frontal plane 110 of user BD, and vertical axis Z1 of user BD and second direction LB are identical when viewed in the direction perpendicular to imaging plane S.

It should be noted that the state in which the initial orientation is obtained is not limited to the above example. A given orientation in which the posture of user BD can be associated with the orientation of intraoral camera 10 may be used. In addition, the posture of user BD may be defined using one or more of frontal plane 110, sagittal plane 111, transverse plane 112, the vertical axis, the sagittal-transverse axis, and the frontal-transverse axis. For instance, part of the state specified above is the state in which axial direction LB of intraoral camera matches vertical axis Z1. However, a state in which axial direction LB of intraoral camera 10 is orthogonal to vertical axis Z1 (a state in which axial direction LB matches the frontal-transverse axis) may be used.

Next, capturing of a tooth image described above is performed. Specifically, area detector 101 adjusts the orientation of intraoral camera 10 obtained when the tooth image was captured, by using the initial orientation (S232). That is, by using the initial orientation, area detector 101 adjusts the orientation of intraoral camera 10 to be the orientation of intraoral camera 10 when the user faces forward.

Figure 20:
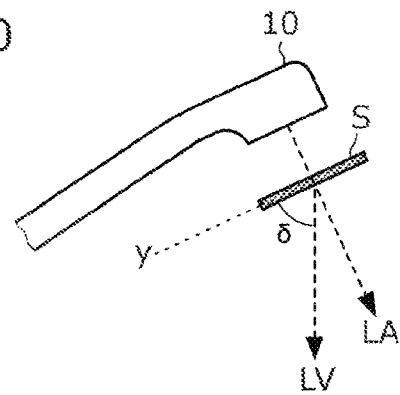
FIG. 20 illustrates an example of the initial orientation according to the variation of the embodiment.
Figure 21:
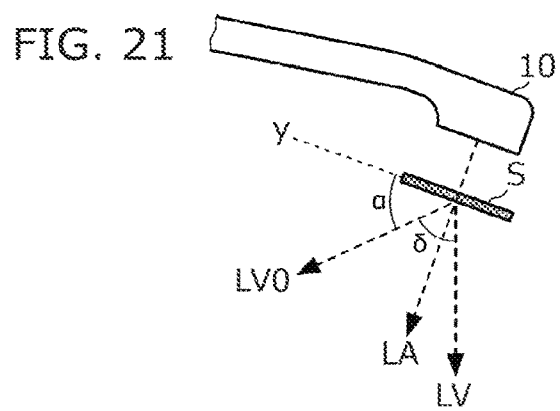
FIG. 21 illustrates an example of adjustment of the orientation according to the variation of the embodiment.

FIG. 20 illustrates an example of the initial orientation. FIG. 21 illustrates an example of adjustment of the orientation. It should be noted that information on the y-axis is adjusted in the following example. However, the same applies to cases in which information on other axes is adjusted. As illustrated in FIG. 20, if angle δ formed by vertical direction LV and the y-axis is obtained as the initial orientation, area detector 101 adjusts vertical direction LV to be vertical direction LV0 as illustrated in FIG. 21. Vertical direction LV0 obtained after the adjustment is used instead of vertical direction LV when, for instance, imaging-direction determination processing is performed. For instance, as illustrated in FIG. 21, an angle formed by vertical direction LV0, which is the direction after the adjustment, and imaging plane S is calculated as angle α formed by vertical direction LV and imaging plane S (y-axis).

It should be noted that instead of adjusting vertical direction LV, area detector 101 may adjust the orientation itself obtained by position sensor 90 or a value being calculated (e.g., angle also used in determination). In addition, part or all of the adjustment processing may be performed by area detector 101 (portable terminal 70) or intraoral camera 10.

Finally, area detector 101 performs the determination of the tooth area and the imaging direction (generates area information) according to the adjusted orientation (S233).

In this manner, area detector 101 can improve determination accuracy by adjusting the orientation of intraoral camera 10 according to the user's posture.

As described above, the intraoral camera system includes the imaging unit (e.g., intraoral camera 10) that generates image data by capturing an image of a tooth inside the mouth of a user, area detector 101 that detects the orientation of the imaging unit according to output by a multi-axis acceleration sensor (e.g., position sensor 90) and detects, according to the detected orientation, an area whose image is being captured by the imaging unit from among areas inside the mouth, the areas being determined by dividing a dentition into sections, and an identifier (103) that narrows candidates which are combinations of tooth types and tooth positions down to fewer candidates to be used, according to the image data and the detected area (e.g., S112 in FIG. 9), and identifies the type and the position of the tooth according to the narrowed candidates and the image data.

Thus, the intraoral camera system determines the target area for image capturing according to the orientation of the imaging unit and identifies the type and position of the tooth by using the determined area. Accordingly, it is possible to reduce the amount of processing and improve the accuracy of identification.

Here, as for the above-mentioned system in which a user manually takes an image, there is a strong request for development of a low-cost miniaturized system. Thus, it is not preferable that a device, such as an optical sensor for detecting the imaging position, be mounted onto the system. Meanwhile, in the embodiment, position sensor 90, such as an acceleration sensor, detects the orientation of the imaging unit and detects an area according to the detected orientation. Accordingly, it is possible to detect an area at low cost and identify a tooth highly accurately by using the detected area.

For instance, as illustrated in, for example, FIG. 6, when detecting the area, area detector 101 detects at least whether the area is a maxillary area or a mandibular area.

For instance, the areas include areas included in a maxillary area and areas included in a mandibular area.

For instance, as illustrated in, for example, FIG. 6, area detector 101 further detects the imaging direction (for example, the buccal side, the lingual side, or the top of the tooth), according to the detected orientation of the imaging unit. Identifier 103 identifies the type and position of the tooth according to the image data and the detected area and imaging direction.

For instance, as illustrated in FIG. 10, identifier 103 calculates the evaluation values (e.g., Err(n)) for respective candidates which are combinations of tooth types and tooth positions, by using the image data (S113). Then, identifier 103 corrects the evaluation values (for example, weights Err(n)) according to the detected area (S118). Then, identifier 103 identifies the type and position of the tooth shown in the image data, by using the corrected evaluation values.

For instance, identifier 103 identifies the type and position of a tooth by using estimation model 106 that includes a neural network (learned model) and outputs the type and position of the tooth when the image data and the detected area are input to estimation model 106.

For instance, identifier 103 detects interdental positions from the image data, generates tooth images each showing a tooth, according to the detected interdental positions, and identifies the type and position of the tooth shown in each of the tooth images, according to the tooth images and the detected area.

For instance, the intraoral camera system further includes user information obtainer 102 that obtains user information indicating at least one of the gender, age group, and race of the user. Identifier 103 identifies the type and position of the tooth according to the user information, the image data, and the detected area.

For instance, as illustrated in FIGS. 13 to 21, the intraoral camera system obtains an initial orientation which is a predetermined orientation of the imaging unit (S231). Area detector 101 adjusts the detected orientation by using the initial orientation (S232) and detects the area whose image is being captured by the imaging unit from the areas (S233).

Thus, the intraoral camera system can improve the accuracy of processing by adjusting the orientation of the imaging unit according to the posture of the user.

For instance, the predetermined orientation is the orientation of the imaging unit when the posture of user BD and the orientation of the imaging unit have a predetermined relationship.

For instance, the imaging unit includes handle 10b, head and neck 10c, head 10a including image sensor 14 that generates image data, neck 10c connecting handle 10b to head and in the predetermined orientation, imaging plane S of the imaging unit is parallel to frontal plane 110 of user BD, and vertical axis Z1 of user BD and the direction from handle 10b toward head 10a are identical or orthogonal when viewed in the direction perpendicular to the imaging plane.

For instance, the imaging unit includes handle 10b, head 10a, and neck 10c, head 10a including image sensor 14 that generates image data, neck 10c connecting handle 10b to head and in the predetermined orientation, a predetermined tooth (for example, anterior tooth) and imaging plane S of the imaging unit are parallel to and face each other, and the direction from handle 10b toward head 10a and a height direction of the predetermined tooth are identical or orthogonal when viewed in the direction perpendicular to imaging plane S.

Thus, the user can readily obtain the initial orientation. In addition, improvement of the accuracy of the initial orientation leads to improvement of the accuracy of adjustment.

The intraoral camera system according to the embodiment of the present disclosure is described above. However, the present disclosure is not limited to the descriptions in the embodiment.

For instance, in the examples described above, intraoral camera 10 mainly used to capture an image of a tooth is used. However, intraoral camera 10 may be an intraoral-care device including a camera. For instance, intraoral camera 10 may be, for example, a dental washer including a camera.

In addition, the processing units included in the intraoral camera system according to the embodiment are typically embodied as LSIs, which are integrated circuits. The processing units may be made as individual chips, or a part or all of the processing units may be incorporated into one chip.

In addition, circuit integration may be achieved not only by an LSI but also by a dedicated circuit or a general-purpose processor. A field programmable gate array (FPGA), which is an LSI that can be programmed after manufacturing or a reconfigurable processor in which the connections and settings of circuit cells inside an LSI are reconfigurable may be used.

In addition, in the embodiment, each of the structural elements may be dedicated hardware or may be caused to function by executing a software program suitable for the structural element. The structural element may be caused to function by a program executer, such as a CPU or a processor, reading and executing a software program stored in a recording medium, such as a hard disk or semiconductor memory.

In addition, the present disclosure may be achieved as, for example, a tooth identification method performed by the intraoral camera system. In addition, the present disclosure may be achieved as the intraoral camera, the portable terminal, or the cloud server included in the intraoral camera system.

In addition, the configuration of the functional blocks illustrated in each block diagram is a mere example. Two or more functional blocks may be incorporated into one functional block. One functional block may be divided into more than one functional block. A part of the function may be transferred from one functional block to another functional block. The same hardware or software may process the functions of two or more functional blocks having similar functions in parallel or on a time-sharing basis.

The order in which the steps are performed in each flowchart is provided as an example to specifically explain the present disclosure. The steps may be performed in a different order. In addition, a part of the steps and another step may be performed simultaneously (in parallel).

The intraoral camera system and the tooth identification method according to one or more aspects are described above on the basis of the embodiment. However, the present disclosure is not limited to the descriptions in the embodiment. Within the scope of the present disclosure, the one or more aspects may include one or more embodiments obtained by making various changes envisioned by those skilled in the art to the embodiment and one or more embodiments obtained by combining structural elements in different embodiments.

INDUSTRIAL APPLICABILITY

The present disclosure is usable in an intraoral camera system.

The invention claimed is:

1. An intraoral camera system comprising:
an imaging unit that generates image data by capturing an image of a tooth inside a mouth of a user;
an orientation detector that detects an orientation of the imaging unit according to output by a multi-axis acceleration sensor;
an area detector that detects, according to the orientation detected, an area whose image is being captured by the imaging unit from among a plurality of areas inside the mouth, the plurality of areas being determined by dividing a dentition into sections; and
an identifier that narrows a plurality of candidates which are combinations of tooth types and tooth positions down to fewer candidates to be used, according to the image data and the area detected, and identifies a type and a position of the tooth according to the fewer candidates narrowed down and the image data,
wherein the identifier:
calculates evaluation values for the plurality of candidates which are the combinations of tooth types and tooth positions, by using the image data,
corrects the evaluation values according to the area detected, and
identifies, by using the evaluation values corrected, the tooth type, imaging direction, and the position of the tooth shown in the image data, and
wherein each candidate being associated with one or more areas among the plurality of areas.

2. The intraoral camera system according to claim 1, wherein when detecting the area, the area detector detects at least whether the area is a maxillary area or a mandibular area.

3. The intraoral camera system according to claim 2, wherein the plurality of areas include areas included in the maxillary area and areas included in the mandibular area.

4. The intraoral camera system according to claim 1, wherein the area detector further detects an imaging direction according to the orientation detected, and
the identifier identifies the type and the position of the tooth according to the image data, the area detected, and the imaging direction detected.

5. The intraoral camera system according to claim 1, wherein the identifier identifies the type and the position of the tooth by using an estimation model that includes a neural network and outputs the type and the position of the tooth when the image data and the area detected are input to the estimation model.

6. The intraoral camera system according to claim 1, wherein the identifier
detects interdental positions from the image data,
generates tooth images each showing a tooth, according to the interdental positions detected, and
identifies a type and a position of the tooth shown in each of the tooth images, according to the tooth images and the area detected.

7. The intraoral camera system according to claim 1, further comprising:
a user information obtainer that obtains user information indicating at least one of a gender, an age group, or a race of the user,
wherein the identifier identifies the type and the position of the tooth according to the user information, the image data, and the area detected.

8. The intraoral camera system according to claim 1, wherein the intraoral camera system obtains an initial orientation which is a predetermined orientation of the imaging unit, and
the area detector adjusts, by using the initial orientation, the orientation detected and detects, according to the orientation adjusted, the area whose image is being captured by the imaging unit from among the plurality of areas.

9. The intraoral camera system according to claim 8, wherein the predetermined orientation is an orientation of the imaging unit when a posture of the user and the orientation of the imaging unit have a predetermined relationship.

10. The intraoral camera system according to claim 9, wherein the imaging unit includes a handle, a head, and a neck, the head including an image sensor that generates image data, the neck connecting the handle to the head, and
in the predetermined orientation, an imaging plane of the imaging unit is parallel to a frontal plane of the user, and a vertical axis of the user and a direction from the handle toward the head are identical or orthogonal when viewed in a direction perpendicular to the imaging plane.

11. The intraoral camera system according to claim 8, wherein the imaging unit includes a handle, a head, and a neck, the head including an image sensor that generates image data, the neck connecting the handle to the head, and
in the predetermined orientation, a predetermined tooth and an imaging plane of the imaging unit are parallel to and face each other, and a direction from the handle toward the head and a height direction of the predetermined tooth are identical or orthogonal when viewed in a direction perpendicular to the imaging plane.

12. A tooth identification method comprising:
generating image data by an imaging unit capturing an image of a tooth inside a mouth of a user;

detecting an orientation of the imaging unit according to output by a multi-axis acceleration sensor and detecting, according to the orientation detected, an area whose image is being captured by the imaging unit from among a plurality of areas inside the mouth, the plurality of areas being determined by dividing a dentition into sections; and narrowing a plurality of candidates which are combinations of tooth types and tooth positions down to fewer candidates to be used, according to the image data and the area detected, and identifying a type and a position of the tooth shown in the image data, according to the fewer candidates narrowed down and the image data, wherein the identifying includes:

calculating evaluation values for the plurality of candidates which are the combinations of tooth types and tooth positions, by using the image data, correcting the evaluation values according to the area detected, and identifying, by using the evaluation values corrected, the tooth type, imaging direction, and the position of the tooth shown in the image data, and wherein each candidate being associated with one or more areas among the plurality of areas.

13. A method of controlling an intraoral camera system including one or more processors and a display, the method comprising:

the following executed by the one or more processors:

obtaining image data generated by an intraoral camera capturing an image of a tooth inside a mouth of a user;

detecting, according to an orientation of the intraoral camera, an area whose image is being captured by the intraoral camera from among a plurality of areas inside the mouth, the plurality of areas being determined by dividing a dentition into sections; and narrowing a plurality of candidates which are combinations of tooth types and tooth positions down to fewer candidates to be used, according to the image data and the area detected, and identifying a type and a position of the tooth shown in the image data, according to the fewer candidates narrowed down and the image data, and displaying, by the display, information on the type and the position of the tooth, wherein the identifying includes:

calculating evaluation values for the plurality of candidates which are the combinations of tooth types and tooth positions, by using the image data, correcting the evaluation values according to the area detected, and identifying, by using the evaluation values corrected, the tooth type, imaging direction, and the position of the tooth shown in the image data, and wherein each candidate being associated with one or more areas among the plurality of areas.

14. A non-transitory computer-readable recording medium having recorded thereon a program for causing a computer to execute the method according to claim 13.

* * * * *